United States Patent
Bonjouklian et al.

(10) Patent No.: US 7,582,652 B2
(45) Date of Patent: Sep. 1, 2009

(54) KINASE INHIBITORS

(75) Inventors: Rosanne Bonjouklian, Zionsville, IN (US); Chafiq Hamdouchi, Carmel, IN (US); Chuan Shih, Carmel, IN (US); Alfonso De Dios, Alcobendas-Madrid (ES); Miriam Filadelfa del Prado, Alcobendas-Madrid (ES); Carlos Jaramillo Aguado, Alcobendas-Madrid (ES); Pramila Kotiyan, Indianapolis, IN (US); Mary Margaret Mader, Fishers, IN (US); Sheila Pleite Selgas, Alcobendas-Madrid (ES); Concepcion Sanchez-Martinez, Alcobendas-Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 571 days.

(21) Appl. No.: 10/597,283

(22) PCT Filed: Jan. 25, 2005

(86) PCT No.: PCT/US2005/000025

§ 371 (c)(1),
(2), (4) Date: Jul. 19, 2006

(87) PCT Pub. No.: WO2005/075478

PCT Pub. Date: Aug. 18, 2005

(65) Prior Publication Data

US 2009/0036445 A1 Feb. 5, 2009

Related U.S. Application Data

(60) Provisional application No. 60/540,830, filed on Jan. 30, 2004.

(51) Int. Cl.
*A01N 43/42* (2006.01)
*A61K 31/44* (2006.01)
*C07D 513/02* (2006.01)
*C07D 515/02* (2006.01)

(52) U.S. Cl. ...................... 514/303; 546/118
(58) Field of Classification Search ............... 546/118; 514/303

See application file for complete search history.

(56) References Cited

U.S. PATENT DOCUMENTS

| | | | |
|---|---|---|---|
| 5,686,455 A | 11/1997 | Adams et al. | |
| 5,717,100 A | 2/1998 | Selnick et al. | |
| 6,335,336 B1 | 1/2002 | Anantanarayan et al. | |
| 6,335,340 B1 | 1/2002 | Gallagher et al. | |
| 6,414,150 B1 | 7/2002 | Adams et al. | |
| 6,426,360 B1 | 7/2002 | Weier et al. | |
| 6,696,434 B2 | 2/2004 | Myers et al. | |
| 6,891,039 B2 * | 5/2005 | Revesz | 544/122 |

FOREIGN PATENT DOCUMENTS

| | | |
|---|---|---|
| WO | WO 96/03387 | 2/1996 |
| WO | WO 99/00130 | 6/1999 |
| WO | WO 00/06563 | 2/2000 |
| WO | WO 01/01988 A1 | 1/2001 |
| WO | WO 01/72737 A1 | 10/2001 |
| WO | WO 02/072579 A1 | 9/2002 |
| WO | WO 02/083111 A2 | 10/2002 |
| WO | WO 03/062215 A1 | 7/2003 |
| WO | WO 2004/013141 A1 | 2/2004 |

* cited by examiner

*Primary Examiner*—D. Margaret Seaman
*Assistant Examiner*—Niloofar Rahmani
(74) *Attorney, Agent, or Firm*—Tina M. Tucker; Robert D. Titus

(57) ABSTRACT

The present invention provides kinase inhibitors of Formula I.

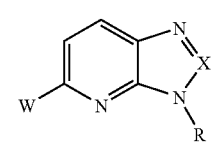

(I)

7 Claims, No Drawings

KINASE INHIBITORS

This application is a Unites States national phase entry, pursuant to 35 U.S.C. 371, of PCT/US2005/000025, filed Jun. 25, 2005, which claims the benefit of U.S. provisional patent application Ser. No. 60/540,830, filed Jan. 30, 2004.

BACKGROUND OF THE INVENTION

The p38 kinase is a mitogen-activated protein (MAP) kinase that belongs to the serine/threonine kinase superfamily. This kinase is activated by extracellular stresses such as heat, UV light, and osmotic stress, as well as by inflammatory stimuli such as lipopolysaccharide. When activated, p38 kinase phosphorylates intracellular protein substrates that regulate the biosynthesis of the pro-inflammatory cytokines tumor necrosis factor α (TNF-α) and interleukin-1β (IL-1β). These cytokines are implicated in the pathology of a number of chronic inflammatory disorders (Lee, et al., *Ann. N.Y. Acad. Sci.*, 696, 149-170 (1993); Muller-Ladner, *Curr. Opin. Rheumatol.*, 8, 210-220 (1996)), cardiovascular and central nervous system disorders (Salituro, et al., *Current Medicinal Chemistry*, 6, 807-823 (1999)), and autoimmune disorders (Pargellis, et al., *Nature Structural Biology*, 9(4), 268-272 (2002)).

A number of compounds within the pyridinylimidazole (WO9621452, WO9725045, U.S. Pat. Nos. 5,656,644, 5,686,455, 5,717,100, WO9712876, WO9821957, WO9847892, WO99903837, WO9901449, WO0061576, WO0172737) and pyrimidinyl-imidazole (WO9725048, WO9901452, WO9725046, WO9932121, WO9901131, WO9901130, WO9901136, WO9807452, WO9747618, WO9856788, WO9857996) structural platforms have been identified as inhibitors of p38 kinase or as cytokine inhibitors. Selective inhibitors of p38 kinase are known to suppress the expression of TNF-α and IL-1β (McKenna, et al., *J. Med. Chem.*, 45(11), 2173-2184 (2002)). Anti-inflammatory activity for compounds within the pyrimidinylimidazole structural platform has been reported (Lantos, et al., *J. Med. Chem.*, 27, 72-75 (1984)), and a number of inhibitors of p38 kinase are under active investigation for the treatment of a variety of disorders (Boehm and Adams, *Exp. Opin. Ther. Patents*, 10(1), 25-37 (2000)). There remains a need for treatment in this field for compounds that are cytokine suppressive drugs, i.e., compounds that are capable of inhibiting p38 kinase.

The present invention provides new inhibitors of p38 kinase useful for the treatment of conditions resulting from excessive cytokine production.

BRIEF SUMMARY OF THE INVENTION

The present invention provides compounds of Formula I:

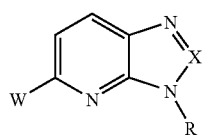

where:
W is:

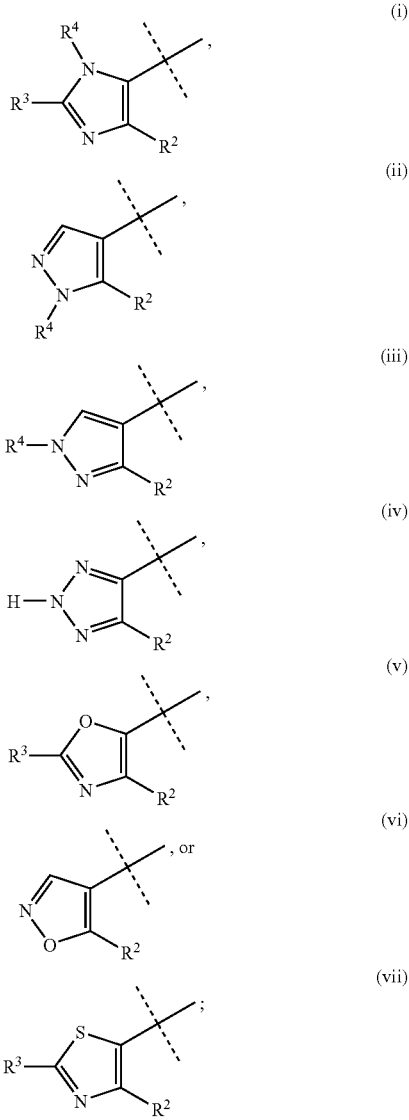

X is N, or C—$R^1$;
R is $C_1$-$C_7$ alkyl, $C_3$-$C_7$ cycloalkyl, ($C_1$-$C_7$ alkylene)-($C_3$-$C_7$ cycloalkyl), —$SO_2$—($C_1$-$C_7$ alkyl), or —$SO_2$—$NR^5R^6$;
$R^1$ is hydrogen, amino, methyl, or —N=CH($NMe$)$_2$;
$R^2$ is phenyl optionally substituted with one or two substituents independently selected from halo;
$R^3$ is hydrogen, $C_1$-$C_7$ alkyl, $C_3$-$C_7$ cycloalkyl, or phenyl optionally substituted with one or two substituents independently selected from halo and trifluoromethyl;
$R^4$ is hydrogen or $C_1$-$C_7$ alkyl;
$R^5$ and $R^6$ are independently selected from the group consisting of $C_1$-$C_7$ alkyl; or a pharmaceutically acceptable salt thereof.

The present invention provides a method of inhibiting β-38 kinase in a mammal comprising administering to a mammal in need of such treatment an effective amount of a compound of Formula I or a pharmaceutically acceptable salt thereof.

The present invention also provides a method of suppressing the production of tumor necrosis factor α (TNF-α) in a mammal comprising administering to a mammal in need of such treatment an effective amount of a compound of Formula I or a pharmaceutically acceptable salt thereof.

The present invention also provides a method of suppressing the production of interleukin-1β (IL-1β) in a mammal comprising administering to a mammal in need of such treatment an effective amount of a compound of Formula I or a pharmaceutically acceptable salt thereof.

The present invention further provides a method of treating conditions resulting from excessive cytokine production in a mammal comprising administering to a mammal in need of such treatment a cytokine-suppressing amount of a compound of Formula I or a pharmaceutically acceptable salt thereof.

The present invention also provides a method of treating a susceptible neoplasm in a mammal comprising administering to a mammal in need of such treatment an effective amount of a compound of Formula I or a pharmaceutically acceptable salt thereof.

The present invention also provides a method of inhibiting metastasis in a mammal comprising administering to a mammal in need of such treatment an effective amount of a compound of Formula I or a pharmaceutically acceptable salt thereof.

The present invention also provides a method of treating rheumatoid arthritis in a mammal comprising administering to a mammal in need of such treatment an effective amount of a compound of Formula I or a pharmaceutically acceptable salt thereof.

The present invention also provides a pharmaceutical formulation comprising a compound of Formula I or a pharmaceutically acceptable salt thereof, in combination with a pharmaceutically acceptable carrier, diluent or excipient.

This invention also provides the use of a compound of Formula I or a pharmaceutically acceptable salt thereof for the manufacture of a medicament for the inhibition of p38 kinase. Additionally, this invention provides a compound of Formula I or a pharmaceutically acceptable salt thereof for use in the inhibition of p38 kinase in mammals. Furthermore, this invention provides a pharmaceutical composition adapted for the inhibition of p38 kinase comprising a compound of Formula I or a pharmaceutically acceptable salt thereof in combination with one or more pharmaceutically acceptable excipients, carriers, or diluents thereof. The invention also provides the use of a compound of Formula I for the manufacture of a medicament for treating a disease or condition capable of being improved or prevented by inhibition of p-38 kinase.

This invention also provides the use of a compound of Formula I or a pharmaceutically acceptable salt thereof for the manufacture of a medicament for the suppression of the production of tumor necrosis factor α (TNF-α). Additionally, this invention provides a compound of Formula I or a pharmaceutically acceptable salt thereof for use in the suppression of the production of tumor necrosis factor α (TNF-α) in mammals. Furthermore, this invention provides a pharmaceutical composition adapted for the suppression of the production of tumor necrosis factor α (TNF-α) comprising a compound of Formula I or a pharmaceutically acceptable salt thereof in combination with one or more pharmaceutically acceptable excipients, carriers, or diluents. The invention also provides the use of a compound of Formula I for the manufacture of a medicament for treating a disease or condition capable of being improved or prevented by suppression of the production of tumor necrosis factor α (TNF-α).

This invention also provides the use of a compound of Formula I or a pharmaceutically acceptable salt thereof for the manufacture of a medicament for the suppression of the production of interleukin-1β (IL-1β). Additionally, this invention provides a compound of Formula I or a pharmaceutically acceptable salt thereof for use in the suppression of the production of interleukin-1β (IL-1β) in mammals. Furthermore, this invention provides a pharmaceutical composition adapted for the suppression of the production of interleukin-1β (IL-1β) comprising a compound of Formula I, or a pharmaceutically acceptable salt thereof, in combination with one or more pharmaceutically acceptable excipients, carriers, or diluents. The invention also provides the use of a compound of Formula I for the manufacture of a medicament for treating a disease or condition capable of being improved or prevented by suppression of the production of interleukin-1β (IL-1β).

This invention also provides the use of a compound of Formula I or a pharmaceutically acceptable salt thereof for the manufacture of a medicament for the treatment of conditions resulting from excessive cytokine production. Additionally, this invention provides a compound of Formula I or a pharmaceutically acceptable salt thereof for use in the treatment of conditions resulting from excessive cytokine production in mammals. Furthermore, this invention provides a pharmaceutical composition adapted for the treatment of conditions resulting from excessive cytokine production comprising a compound of Formula I or a pharmaceutically acceptable salt thereof in combination with one or more pharmaceutically acceptable excipients, carriers, or diluents. The invention also provides the use of a compound of Formula I for the manufacture of a medicament for treating a disease or condition capable of being improved or prevented by suppression of excessive cytokine production.

This invention also provides the use of a compound of Formula I or a pharmaceutically acceptable salt thereof for the manufacture of a medicament for the treatment of a susceptible neoplasm. Additionally, this invention provides a compound of Formula I or a pharmaceutically acceptable salt thereof for use in the treatment of a susceptible neoplasm in mammals. Furthermore, this invention provides a pharmaceutical composition adapted for the treatment of a susceptible neoplasm comprising a compound of Formula I or a pharmaceutically acceptable salt thereof in combination with one or more pharmaceutically acceptable excipients, carriers, or diluents.

This invention also provides the use of a compound of Formula I or a pharmaceutically acceptable salt thereof for the manufacture of a medicament for the inhibition of metastasis. Additionally, this invention provides a compound of Formula I or a pharmaceutically acceptable salt thereof for use in the inhibition of metastasis in mammals. Furthermore, this invention provides a pharmaceutical composition adapted for the inhibition of metastasis comprising a compound of Formula I or a pharmaceutically acceptable salt thereof in combination with one or more pharmaceutically acceptable excipients, carriers, or diluents.

This invention also provides the use of a compound of Formula I or a pharmaceutically acceptable salt thereof for the manufacture of a medicament for the treatment of rheumatoid arthritis. Additionally, this invention provides a compound of Formula I or a pharmaceutically acceptable salt thereof for use in the treatment of rheumatoid arthritis in mammals. Furthermore, this invention provides a pharmaceutical composition adapted for the treatment of rheumatoid arthritis comprising a compound of Formula I or a pharmaceutically acceptable salt thereof in combination with one or more pharmaceutically acceptable excipients, carriers, or diluents.

DETAILED DESCRIPTION OF THE INVENTION

The general chemical terms used in the formulae above have their usual meanings. For example, the term "$C_1$-$C_7$ alkyl" includes methyl, ethyl, propyl, isopropyl, butyl, isobutyl, sec-butyl, tert-butyl, pentyl, hexyl and heptyl moieties. The term "$C_1$-$C_7$ alkylene" includes methylene, ethylene, propylene, isopropylene, butylene, isobutylene, sec-butylene, tert-butylene, pentylene, hexylene and heptylene moieties. The term "$C_3$-$C_7$ cycloalkyl" includes cyclopropyl, cyclobutyl, cyclopentyl, cyclohexyl and cycloheptyl moieties. The term "($C_1$-$C_7$ alkylene)-($C_3$-$C_7$ cycloalkyl)" is taken to mean a $C_3$-$C_7$ cycloalkyl attached through a $C_1$-$C_7$ alkylene linker. The term "halo" includes fluoro, chloro, bromo, and iodo.

The term "p-38 kinase" is taken to mean the p-38α and/or p-38β kinase isoforms.

The term "suppressing the production of TNF-α (IL-1β, cytokine)" is taken to mean decreasing of excessive in vivo levels of TNF-α, IL-1β, or another cytokine in a mammal to normal or sub-normal levels. This may be accomplished by inhibition of the in vivo release of TNF-α, IL-1β, or another cytokine by all cells, including macrophages; by down regulation, at the genomic level, of excessive in vivo levels of TNF-α, IL-1β, or another cytokine in a mammal to normal or sub-normal levels; by inhibition of the synthesis of TNF-α, IL-1β, or another cytokine as a posttranslational event; or by a down regulation of TNF-α, IL-1β, or another cytokine at the translational level.

The term "Minimum Effective Dose (MED)" is taken to mean the smallest dose that produces an effect that is statistically significantly different from the effect observed in a vehicle control group.

The term "Threshold Effective Dose (TED)" is taken to mean the dose required to achieve a specified threshold of activity. For example, the $TED_{50}$ is the dose required to achieve a response of 50%.

The term "Threshold Minimum Effective Dose (TMED)" is taken to mean the lowest dose that guarantees a statistically significant effect that also achieves a specified threshold level of activity. For example, the $TMED_{50}$ is the lowest dose that achieves a 50% response and is certain to be statistically significantly different from a vehicle control group.

The term "effective amount" is taken to mean a dose of a compound of Formula I necessary to achieve the desired pharmacological effect.

The skilled artisan will appreciate that certain compounds of Formula I contain at least one chiral center. The present invention contemplates all individual enantiomers or diastereomers, as well as mixtures of the enantiomers and diastereomers of said compounds including racemates. It is preferred that compounds of Formula I containing at least one chiral center exist as single enantiomers or diastereomers. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques.

The skilled artisan will also appreciate that when variable "W" is imidazole (i), and $R^4$ is hydrogen, the imidazole ring exists in the following two tautomeric forms:

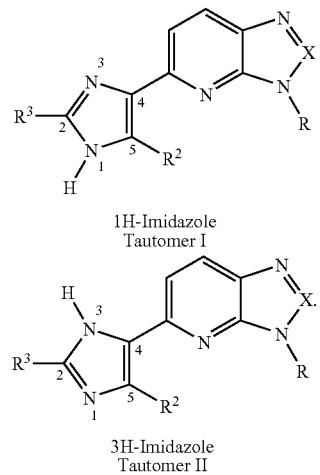

1H-Imidazole
Tautomer I

3H-Imidazole
Tautomer II

Although Tautomers I and II are structurally distinct, the skilled artisan will appreciate that they exist in equilibrium and are easily and rapidly interconvertible under ordinary conditions. (See: March, *Advanced Organic Chemistry*, Third Edition, Wiley Interscience, New York, N.Y. (1985), pages 66-70; and Allinger, *Organic Chemistry*, Second Edition, Worth Publishers, New York, N.Y., (1976), page 173) As such, the representation of a compound of Formula I, where variable "W" is imidazole (i) and $R^4$ is hydrogen, in one tautomeric form contemplates both tautomeric forms of the imidazole ring. Likewise, the naming of a compound of Formula I where "W" is imidazole (i) and $R^4$ is hydrogen as either a 1H-imidazole or a 3H-imidazole contemplates both tautomeric forms of the imidazole ring. Specifically, the name 5-[2-tert-butyl-5-(4-fluoro-phenyl)-1H-imidazol-4-yl]-3-(2,2-dimethyl-propyl)-3H-imidazo[4,5-b]pyridin-2-ylamine contemplates the molecule in either the 1H-imidazol-4-yl or 3H-imidazol-4-yl form. Similarly, when variable "W" is triazole (iv), the triazole moiety exists in three tautomeric forms, and the representation or naming of one tautomeric form contemplates all three tautomeric forms of the triazole ring.

It will be understood by the skilled reader that compounds of the present invention are capable of forming salts. In all cases, the pharmaceutically acceptable salts of all of the compounds are included in the names of them. The compounds of the present invention are amines, and accordingly react with any of a number of inorganic and organic acids to form pharmaceutically acceptable acid addition salts. Preferred pharmaceutically acceptable salts are those formed with maleic acid, fumaric acid, succinic acid, hydrochloric acid, and methanesulfonic acid. Especially preferred are di-methanesulfonic acid salts of the compounds of Formula I.

Certain classes of compounds of Formula I are preferred inhibitors of p-38 kinase. The following paragraphs describe such preferred classes:

a) W is:

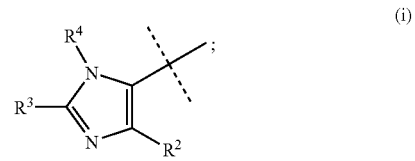

(i)

b) W is:

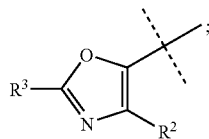
(v)

c) X is C—$R^1$;
d) X is C—$NH_2$;
e) $R^2$ is phenyl, 4-fluorophenyl, or 2,4-difluorophenyl;
f) $R^2$ is phenyl;
g) $R^2$ is 4-fluorophenyl;
h) $R^2$ is 2,4-difluorophenyl;
i) $R^4$ is hydrogen;
j) W is

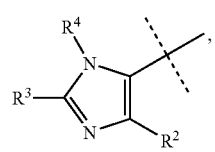
(i)

X is C—$R^1$, $R^2$ is phenyl, 4-fluorophenyl, or 2,4-difluorophenyl, and $R^4$ is hydrogen;

k) W is

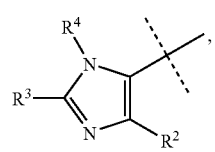
(i)

X is C—$NH_2$, $R^2$ is phenyl, 4-fluorophenyl, or 2,4-difluorophenyl, and $R^4$ is hydrogen;

l) W is

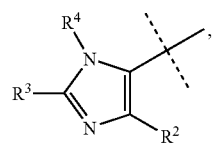
(i)

X is C—$R^1$, R is $C_1$-$C_7$ alkyl, $R^2$ is phenyl, 4-fluorophenyl, or 2,4-difluorophenyl, $R^3$ is $C_1$-$C_7$ alkyl or phenyl optionally substituted with one or two substituents independently selected from halo and trifluoromethyl, and $R^4$ is hydrogen;

m) W is

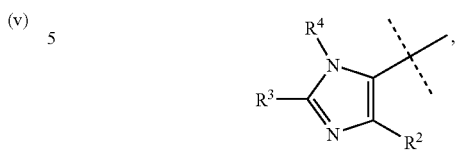
(i)

X is C—$NH_2$, R is $C_1$-$C_7$ alkyl, $R^2$ is phenyl, 4-fluorophenyl, or 2,4-difluorophenyl, $R^3$ is $C_1$-$C_7$ alkyl or phenyl optionally substituted with one or two substituents independently selected from halo, and $R^4$ is hydrogen;

n) The compound of Formula I is a free base.
o) The compound of Formula I is a salt.
p) The compound of Formula I is a methanesulfonate salt.
q) The compound of Formula I is a di-methanesulfonate salt.

Preferred embodiments of the present invention include all combinations of paragraphs a)-q).

An especially preferred subgenus of compounds within the scope of Formula I are compounds of Formula I':

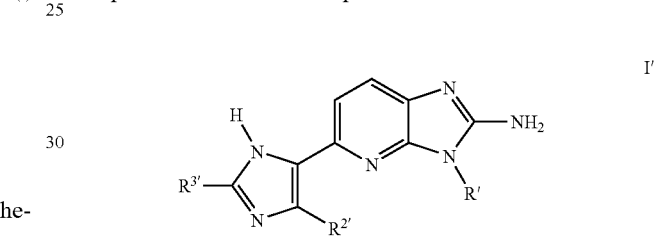
I' where:
R' is 2,2-dimethylpropyl or 1,2,2-trimethylpropyl;
$R^{2'}$ is phenyl, 4-fluorophenyl, or 2,4-difluorophenyl;
$R^{3'}$ is tert-butyl, 2-chloro-6-fluorophenyl, 2-fluoro-6-trifluoromethylphenyl, 2,6-dichlorophenyl, or 2,6-difluorophenyl; or a pharmaceutically acceptable salt thereof.

Most preferred compounds of Formula I' are those where:
1. R' is 2,2-dimethylpropyl, $R^{2'}$ is 4-fluorophenyl, and $R^{3'}$ is 2-fluoro-6-trifluoromethylphenyl;
2. R' is 2,2-dimethylpropyl, $R^{2'}$ is 4-fluorophenyl, and $R^{3'}$ is 2,6-dichlorophenyl;
3. R' is 2,2-dimethylpropyl, $R^{2'}$ is 4-fluorophenyl, and $R^{3'}$ is tert-butyl;
4. R' is 2,2-dimethylpropyl, $R^{2'}$ is phenyl, and $R^{3'}$ is 2-chloro-6-fluorophenyl;
5. R' is 2,2-dimethylpropyl, $R^{2'}$ is 2,6-difluorophenyl, and $R^{3'}$ is tert-butyl;
6. R' is 1,2,2-trimethylpropyl, $R^{2'}$ is 4-fluorophenyl, and $R^{3'}$ is tert-butyl; and
7. R' is 1,2,2-trimethylpropyl, $R^{2'}$ is 4-fluorophenyl, and $R^{3'}$ is 2,6-difluorophenyl.

It is also preferred that each of these compounds exist as the methanesulfonate, succinate, fumarate, dimaleate, dihydrochloride, or dimethanesulfonate salt. It is especially preferred that each of these compounds exist as the dimethanesulfonate salt.

The compounds of Formula I are inhibitors of p38 kinase. Thus, the present invention also provides a method of inhibiting p38 kinase in a mammal that comprises administering to a mammal in need of said treatment an effective amount of a compound of Formula I. It is preferred that the mammal to be treated by the administration of the compounds of Formula I is human.

As inhibitors of p38 kinase, the compounds of the present invention are useful for suppressing the production of the pro-inflammatory cytokines tumor necrosis factor α (TNF-α) and interleukin-1β (IL-1β), and therefore for the treatment of disorders resulting from excessive cytokine production. Compounds of Formula I are therefore believed to be useful in treating inflammatory disorders, including eczema, atopic dermatitis, rheumatoid arthritis, osteoarthritis, inflammatory bowel disease, and toxic shock syndrome. Compounds of the present invention are also believed to be useful in the treatment of cardiovascular disorders, such as acute myocardial infarction, chronic heart failure, atherosclerosis, viral myocarditis, cardiac allograft rejection, and sepsis-associated cardiac dysfunction. Furthermore, compounds of the present invention are also believed to be useful for the treatment of central nervous system disorders, such as meningococcal meningitis, Alzheimer's disease, Parkinson's disease, and multiple sclerosis.

Most solid tumors increase in mass through the proliferation of malignant cells and stromal cells, including endothelial cells. In order for a tumor to grow larger than 2-3 millimeters in diameter, it must form a vasculature, a process known as angiogenesis. Suppression of tumor-induced angiogenesis by angiostatin and endostatin has been reported to result in antitumor activity (O'Reilly, et al., *Cell*, 88, 277-285 (1997)). The selective p38 kinase inhibitor SB22025 has been shown to inhibit angiogenesis (J. R. Jackson, et al., *J. Pharmacol. Exp. Therapeutics*, 284, 687 (1998)). Because angiogenesis is a critical component of the mass expansion of most solid tumors, the development of new p38 kinase inhibitors for the inhibition of this process represents a promising approach for antitumor therapy. This approach to antitumor therapy may lack the toxic side effects or drug resistance-inducing properties of conventional chemotherapy (Judah Folkman, *Endogenous Inhibitors of Angiogenesis*, The Harvey Lectures, Series 92, pages 65-82, Wiley-Liss Inc., (1998)).

As inhibitors of p38 kinase, compounds of the present invention, therefore, are also useful in inhibiting growth of susceptible neoplasms. Schultz, R. M. *Potential of p38 MAP kinase inhibitors in the treatment of cancer.* In: E. Jucker (ed.), *Progress in Drug Research*, 60, 59-92, (2003). A susceptible neoplasm is defined to be a neoplasm that depends upon p38 kinase for its survival, growth, or metastasis. Susceptible neoplasms include tumors of the brain, genitourinary tract, lymphatic system, stomach, larynx, and lung (U.S. Pat. No. 5,717,100). Preferably, the term "susceptible neoplasms" as used in the present application includes human cancers including non-small cell lung carcinoma (A. Greenberg, et al., *Am. J. Respir. Cell Mol. Biol.*, 26, 558 (2002)), breast carcinoma (J. Chen, et al., *J. Biol. Chem.*, 276, 47901 (2001); B. Salh, et al., *Int. J. Cancer*, 98, 148 (2002); and S. Xiong, et al., *Cancer Res.*, 61, 1727 (2001)), gastric carcinoma (Y. D. Jung, et al., *Proc. Am. Assoc. Cancer Res.*, 43, 9 (2002)), colorectal carcinomas (S. Xiong, et al., *Cancer Res.*, 61, 1727 (2001)), prostate carcinomas (J-I Park, et al., *Oncogene*, 22, 4314-4332 (2003); L. Chen, et al., *Cancer Lett.*, 215, 239-247 (2004); and A. R. Uzgara, et al., *Prostate*, 55, 128-139 (2003)), malignant melanoma (C. Denkert, et al., *Clin. Exp. Metastasis*, 19, 79 (2002)), and multiple myeloma (Hideshima, et al., *Oncogene advance online publication*, 1-11, (11 Oct. 2004); and Hideshima, et al., *Blood*, 101(2), 703 (2003)).

Inhibition of angiogenesis by suppression of TNF-α has also been taught to be useful in the inhibition or prevention of metastasis (U.S. Pat. Nos. 6,414,150; 6,335,336). Furthermore, suppression of TNF-α is indicated for the treatment and prevention of cachexia, a wasting syndrome experienced by about half of all cancer patients (T. Yoneda, et al., *J. Clin. Invest.*, 87, 977 (1991)).

Furthermore, inhibition of p38 kinase may be effective in the treatment of certain viral conditions such as influenza (K. Kujime, et al., *J. Immunology.*, 164, 3222-3228 (2000)), rhinovirus (S. Griego, et al., *J. Immunology*, 165, 5211-5220 (2000)), and HIV (L. Shapiro, et al., *Proc. Natl. Acad. Sci. USA*, 95, 7422-7426, (1998)).

The compounds of the present invention may be prepared by a variety of procedures, some of which are illustrated in the Schemes below. It will be recognized by one of skill in the art that the individual steps in the following schemes may be varied to provide the compounds of Formula I. The particular order of steps required to produce the compounds of Formula I is dependent upon the particular compound being synthesized, the starting compound, and the relative lability of the substituted moieties. Some substituents have been eliminated in the following schemes for the sake of clarity and are not intended to limit the teaching of the schemes in any way.

Compounds of Formula I where W is the imidazole (i) may be prepared as illustrated in the following scheme where R, $R^1$, $R^2$, and $R^3$ are as previously defined.

Scheme I

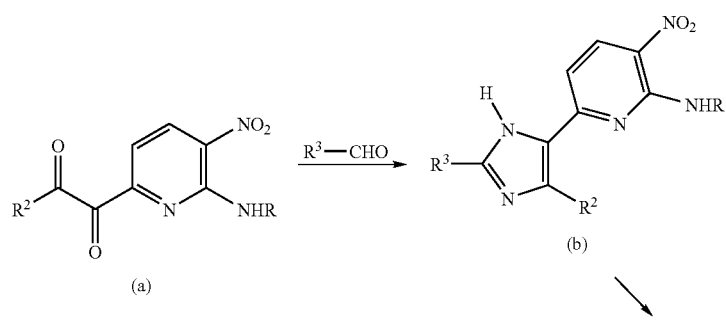

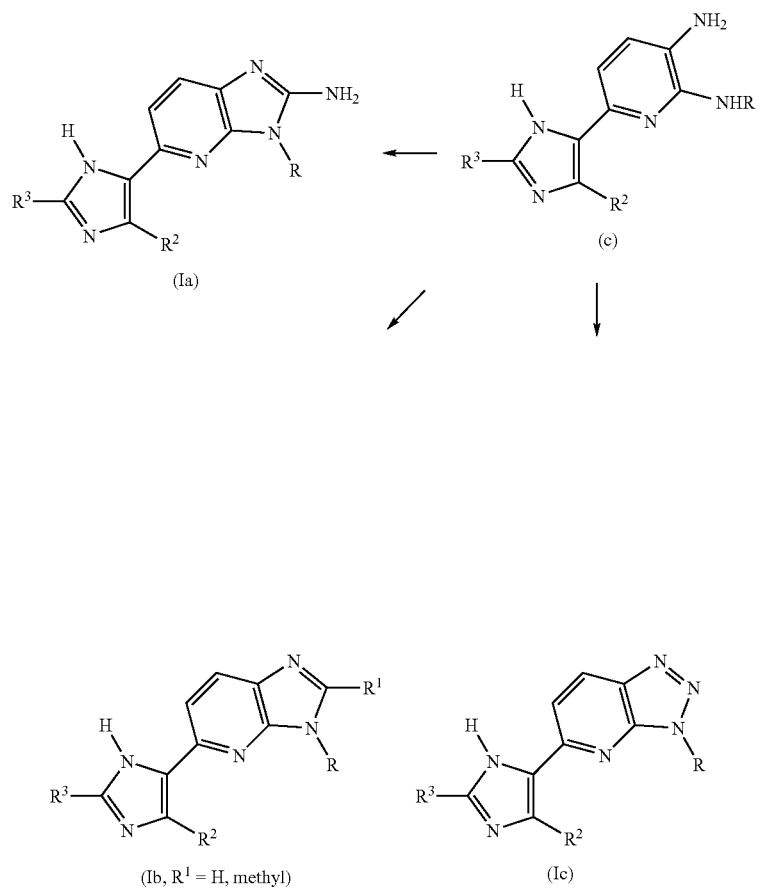

Diketone (a) is reacted with ammonium acetate and an appropriate aldehyde in an appropriate solvent, preferably acetic acid, to provide the corresponding nitropyridinyl-imidazole (b). The nitro moiety is reduced under standard hydrogenation or chemical conditions to provide the corresponding diamine (c). This diamine is then either reacted with cyanogen bromide to provide the 3-substituted-5-(imidazol-4-yl)-2-aminopyridinyl-imidazole (Ia), with an appropriate orthoformate to provide the 3-substituted-5-(imidazol-4-yl) pyridinylimidazole (Ib), or with an appropriate nitrite to provide the 3-substituted-5-(imidazol-4-yl)pyridinyltriazole (Ic).

The requisite diketones (a) may be prepared as described in the following scheme, where R and $R^2$ are as previously defined.

Scheme II

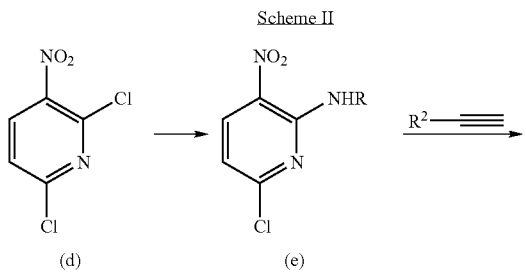

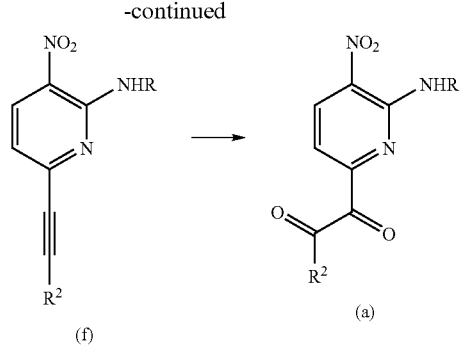

2,6-dichloronitropyridine (d) and an appropriate amine or amine derivative are heated together in an appropriate solvent to provide the corresponding 2-amino-6-chloro-3-nitropyridine (e), which is then coupled with an appropriately substituted acetylene to provide the corresponding 1,2-disubstituted acetylene (f). This acetylene is oxidized to provide the target diketone (a).

Compounds of Formula I where W is pyrazole (ii) or (iii) are prepared as described in the following Scheme where X, R, $R^1$, and $R^2$ are as previously defined.

Scheme III

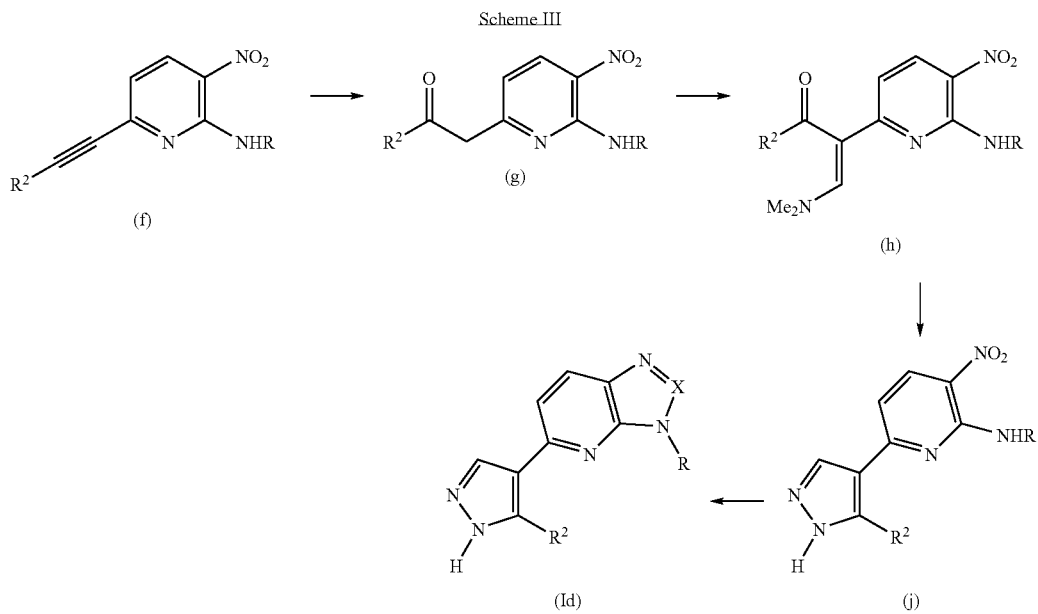

Acetylene (f) is treated with mercuric oxide in aqueous sulfuric acid to provide the ketone (g). This ketone is treated with dimethylformamide dimethylacetal or tris(dimethylamino)methane in a suitable solvent, typically dimethylformamide, to provide the enaminoketone (h). The enaminoketone is then treated with hydrazine in a suitable solvent, typically ethanol or methanol, to provide the phenylpyrazole (j). The imidazo- or triazolopyridine moiety is prepared as previously described to provide the compounds of Formula Id.

The compounds of Formula I where W is the [1,2,3]triazole (iv) may be prepared as described in the following Scheme where variables Y, R, and $R^2$ are as previously defined.

Scheme IV

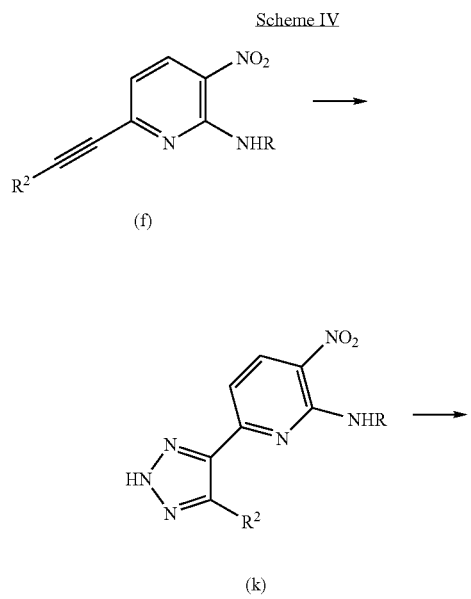

-continued

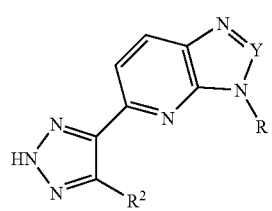

The acetylene (f) is reacted with a source of azide, typically sodium azide, in a suitable solvent, such as dimethyoxyethane to provide the triazole (k). The imidazo- or triazolopyridine moiety is prepared as previously described to provide the compounds of Formula Ie.

The compounds of Formula I where W is the thiazole (v) or oxazole (vii) may be prepared as described in the following Scheme where variables X, R, $R^2$, and $R^3$ are as previously defined and Y is O or S.

Scheme V

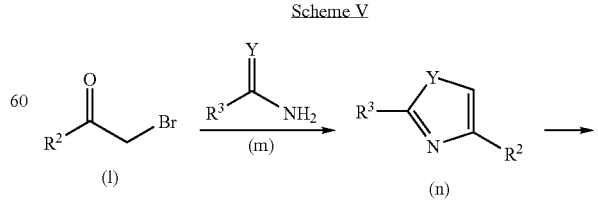

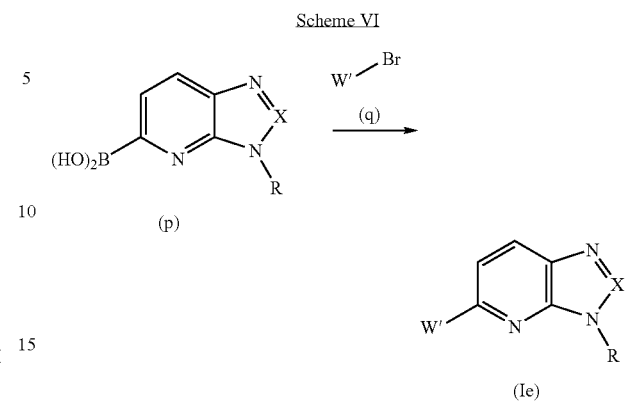

Scheme VI

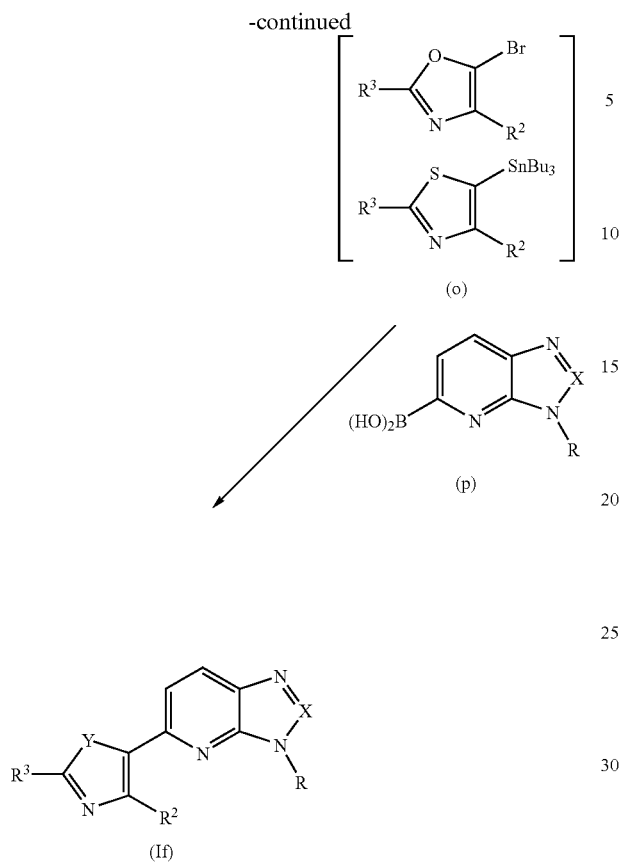

The α-bromoketone (l) is reacted with an appropriate amide (m, Y=O) or thioamide (m, Y=S) in a suitable solvent to provide the corresponding oxazole or thiazole (n). The oxazole (m, Y=O) is then treated with bromine in a suitable solvent to provide the corresponding brominated heterocycle (o, Y=O). The thiazole (m, Y=S) is treated with n-butyllithium and the resulting anion reacted with tributyltin chloride to provide the corresponding tin derivative (o, Y=S). The appropriately substituted heterocycle (o) is reacted with an appropriate boronic acid (p) in the presence of a suitable catalyst as previously described to provide the compounds of Formula If.

The requisite α-bromoketones are either commercially available or may be prepared by standard conditions from the corresponding carbonyl compound, for example, as described by House (H. O. House, *Modern Synthetic Reactions*, W.A. Benjamin, Inc., Menlo Park, Calif. (1972), pages 459-478) and Larock (R. C. Larock, *Comprehensive Organic Transformations*, VCH Publishers, Inc., New York, N.Y. (1989), pages 369-471, 755). The requisite amides and thioamides are either commercially available or may be prepared by standard methods well known to the skilled artisan.

Additional compounds of Formula I where W is imidazole (i) or isoxazole (vi) may be prepared under standard palladium coupling conditions as described in the following Scheme, where W' is imidazole (i) or isoxazole (vi), and X and R are as previously defined.

An appropriately substituted haloheteroaryl (q) is coupled with an appropriately substituted boronic acid (p) in the presence of a palladium catalyst, typically bis(triphenylphosphine)palladium(II) chloride, in a suitable solvent to provide the desired compound of Formula Ie. The requisite starting materials are either commercially available or may be prepared by methods well known to one of ordinary skill in the art.

Many of the compounds of the present invention are not only useful as inhibitors of p38 kinase, but are also useful intermediates for the preparation of additional compounds of the present invention. For example, primary and secondary amines may be acylated, alkylated or coupled with carboxylic acids or amino acids under standard peptide coupling conditions. Furthermore, ester moieties may be reduced to the corresponding alcohols or converted to amides under standard conditions. Alcohols may be activated and displaced by a number of nucleophiles to provide other compounds of the invention. Such leaving groups include but are not limited to halides, oxonium ions, alkyl perchlorates, ammonioalkanesulfonate esters, alkyl fluorosulfonates, nonaflates, tresylates, triflates, and sulfonic esters, preferably the mesylate or tosylate. Techniques for the introduction of these groups are also well known to the skilled artisan; see, for example, March, *Advanced Organic Chemistry*, 5th Ed., John Wiley and Sons, New York, pg. 445-449 (2001). Additionally, the 2-amino moiety of the benzimidazole nucleus may be diazotized and displaced to provide additional compounds of the invention under standard conditions.

The skilled artisan will also appreciate that not all of the substituents in the compounds of Formula I will tolerate certain reaction conditions employed to synthesize the compounds. These moieties may be introduced at a convenient point in the synthesis, or may be protected and then deprotected as necessary or desired. The skilled artisan will appreciate that the protecting groups may be removed at any convenient point in the synthesis of the compounds of the present invention. Methods for introducing and removing nitrogen and oxygen protecting groups are well known in the art; see, for example, Greene and Wuts, *Protective Groups in Organic Synthesis*, 3rd Ed., John Wiley and Sons, New York, Chapter 7 (1999). Furthermore, the skilled artisan will appreciate that in many circumstances, the order in which moieties are introduced is not critical. The particular order of steps required to produce the compounds of Formula I is dependent upon the particular compound being synthesized, the starting compound, and the relative lability of the substituted moieties.

The abbreviations, symbols and terms used in the examples and assays have the following meanings: AcOH=acetic acid; DMF=N,N-dimethylformamide; DMSO=dimethylsulfoxide; $Et_2O$=diethyl ether; EtOAc=ethyl acetate; EtOH=ethanol; h=hour(s); MeOH=methanol; min=minute(s); MTBE=methyl tert-butyl ether; $Pd(OAc)_2$=palladium acetate; RT=room temperature; THF=tetrahydrofuran; $VO(acac)_2$=vanadyl acetylacetonate.

Preparation 1

[6-(2-tert-Butyl-5-phenyl-3H-imidazol-4-yl)-3-nitro-pyridin-2-yl]-(2,2-dimethylpropyl)amine (6-Chloro-3-nitropyridin-2-yl)-(2,2-dimethyl-propyl)amine Add neopentylamine (18 mL, 150 mmol) to a suspension of 2,6-dichloro-3-nitropyridine (20 g, 103 mmol) and $Na_2CO_3$ (18.5 g, 175 mmol) in EtOH (1.6 mL/mmol) at RT and stir overnight. Concentrate and dilute the resultant slurry with water (100 mL) and slowly neutralize with concentrated HCl (approx. 40 mL) to pH=7. Cool the suspension at 0° C. for 1 h and collect solid by vacuum filtration. Wash the solid with ice water (4×50 mL) and air dry overnight. Recrystallize the material from EtOAc and hexanes to give the title compound as a yellow solid (21.23 g, 84%).

MS (ES): m/z=244 [M+H]

(2,2-Dimethylpropyl)-(3-nitro-6-phenylethynylpyridin-2-yl)amine

Dissolve (6-chloro-3-nitropyridin-2-yl)-(2,2-dimethylpropyl)amine (7.3 g, 30.0 mmol), phenylacetylene (5.0 mL, 45 mmol) and triphenylphosphine (1.5 mmol, 0.39 g) in triethylamine (10 mL/g) in an oven-dried round bottom flask is flushed with nitrogen and evacuated three times. Add $Pd(OAc)_2$ (0.10 g, 0.45 mmol) and the nitrogen flush/evacuation cycle is repeated (3×). Heat at 70-80° C. with stirring under nitrogen for 1-3 h, then cool at RT for 2 h. Concentrate and partition between water (25 mL) and EtOAc (150 mL). Separate the organic layer and wash with water (4×25 mL), saturated aqueous NaCl (25 mL), dry with $MgSO_4$, filter, and concentrate. Purify the crude solid by recrystallization from EtOAc/hexanes to give the title product as a bright orange solid (6.5 g, 21.2 mmol, 71%).

MS (ES): m/z=310 [M+H]; mp 90-92° C.

1-[6-(2,2-Dimethylpropylamino)-5-nitropyridin-2-yl]-2-phenylethane-1,2-dione

Cool a mixture of (2,2-dimethylpropyl)-(3-nitro-6-phenylethynylpyridin-2-yl)amine (3.11 g, 10 mmol), $NaHCO_3$ (0.420 g, 5.0 mmol), $MgSO_4$ (2.40 g, 20 mmol) in acetone (85 mL), and water (25 mL) and cool to 0° C. Add $KMnO_4$ (3.16 g, 20.0 mmol) to the cooled mixture, and stir the reaction mixture vigorously at 0° C. for about 1-2 h. Quench the mixture with $Na_2SO_3$ (5.67 g, 45 mmol). Remove ice bath and stir mixture at RT for 2 h. Filter the solid through a pad of filtering agent. Wash with water (2×50 mL) and EtOAc (50 mL). Separate the phases and extract the aqueous phase with EtOAc (3×50 mL). Wash the combined organic phases with saturated aqueous NaCl (25 mL), dry with $MgSO_4$, filter and concentrate. Purify the crude (silica gel chromatography, eluting with 1:1 hexanes:$CH_2Cl_2$) to give the title compound (1.586 g, 46%).

MS (ES): m/z=342 [M+H]; mp 88-90° C.

[6-(2-tert-Butyl-5-phenyl-3H-imidazol-4-yl)-3-nitro-pyridin-2-yl]-(2,2-dimethylpropyl)amine Heat a mixture of 1-[6-(2,2-dimethylpropylamino)-5-nitropyridin-2-yl]-2-phenylethane-1,2-dione (1.0241 g, 3.0 mmol), trimethylacetaldehyde (0.66 mL, 6.0 mmol), ammonium acetate (3.47 g, 45 mmol) in AcOH (5 mL/mmol) at 80° C. with monitoring by liquid chromatography—mass spectroscopy for the appearance of product. Cool the reaction mixture to 0° C. and neutralize to pH 7 with 5.0 N NaOH. Extract the neutralized aqueous phase with EtOAc (3×20 mL) and wash the combined organic phases with 20 mL portions of saturated aqueous $NaHCO_3$ until no further neutralization is observed. Dry the organic phase with $MgSO_4$, filter, and concentrate. Triturate the orange crude solid with EtOAc to obtain the title compound (0.7578 g, 62%).

MS (ES): m/z=408 [M+H]; mp 224-226° C.

The compounds of Preparations 2-21 may be prepared essentially as described in Preparation 1.

| Prep. | Compound | MS (ES): m/z [M + H] |
|---|---|---|
| 2 | {6-[2-(2,6-Difluorophenyl)-5-phenyl-3H-imidazol-4-yl]-3-nitropyridin-2-yl}-(2,2-dimethylpropyl)amine | 464 |
| 3 | {6-[2-(2,6-Dichlorophenyl)-5-phenyl-3H-imidazol-4-yl]-3-nitropyridin-2-yl}-(2,2-dimethylpropyl)amine | 496 |
| 4 | {6-[2-(2-Chloro-6-fluorophenyl)-5-phenyl-3H-imidazol-4-yl]-3-nitropyridin-2-yl}-(2,2-dimethylpropyl)amine | 480 |
| 5 | (2,2-Dimethylpropyl){6-[5-(4-fluorophenyl)-2-isopropyl-3H-imidazol-4-yl]-3-nitropyridin-2-ylamine | 412 |
| 6 | Cyclopropylmethyl{6-[2-(2,6-difluorophenyl)-5-phenyl-3H-imidazol-4-yl]-3-nitropyridin-2-ylamine | 448 |
| 7 | Cyclopropylmethyl{6-[2-(2,6-dichlorophenyl)-5-phenyl-3H-imidazol-4-yl]-3-nitropyridin-2-ylamine | 480 |
| 8 | Cyclopropylmethyl{6-[2-(2,6-difluorophenyl)-5-(4-fluorophenyl)-3H-imidazol-4-yl]-3-nitropyridin-2-ylamine | 466 |
| 9 | Cyclopropylmethyl{6-[2-(2,6-dichlorophenyl)-5-(4-fluorophenyl)-3H-imidazol-4-yl]-3-nitropyridin-2-ylamine | 498 |
| 10 | Cyclopropylmethyl{6-[5-(4-fluorophenyl)-2-isopropyl-3H-imidazol-4-yl]-3-nitropyridin-2-ylamine | 396 |
| 11 | [6-(2-tert-Butyl-5-phenyl-3H-imidazol-4-yl)-3-nitropyridin-2-yl]cyclopropylmethylamine | 392 |

-continued

| Prep. | Compound | MS (ES): m/z [M + H] |
|---|---|---|
| 12 | {6-[2-(2,6-Difluorophenyl)-5-(4-fluorophenyl)-3H-imidazol-4-yl]-3-nitropyridin-2-yl}-(2,2-dimethylpropyl)amine | 482 |
| 13 | {6-[2-tert-Butyl-5-(4-fluorophenyl)-3H-imidazol-4-yl]-3-nitropyridin-2-yl}cyclopropylmethylamine | 410 |
| 14 | [6-(2-Cyclopropyl-5-phenyl-3H-imidazol-4-yl)-3-nitropyridin-2-yl]-(2,2-dimethylpropyl)amine | 392 |
| 15 | (2,2-Dimethylpropyl)-{6-[5-(4-fluorophenyl)-2-(2-fluoro-6-trifluoromethylphenyl)-3H-imidazol-4-yl]-3-nitropyridin-2-ylamine | 532 |
| 16 | (2,2-Dimethylpropyl)-{6-[2-(2-fluoro-6-trifluoromethylphenyl)-5-phenyl-3H-imidazol-4-yl]-3-nitropyridin-2-ylamine | 514 |
| 17 | {6-[2-Cyclopropyl-5-(4-fluorophenyl)-3H-imidazol-4-yl]-3-nitropyridin-2-yl}-(2,2-dimethylpropyl)amine | 410 |
| 18 | {6-[2-(2,6-Dichlorophenyl)-5-(4-fluorophenyl)-3H-imidazol-4-yl]-3-nitropyridin-2-yl}-(2,2-dimethylpropyl)amine | 514 |
| 19 | {6-[2-tert-Butyl-5-(4-fluorophenyl)-3H-imidazol-4-yl]-3-nitropyridin-2-yl}-(2,2-dimethylpropyl)amine | 426 |
| 20 | {6-[2-tert-Butyl-5-(2,4-difluorophenyl)-3H-imidazol-4-yl]-3-nitropyridin-2-yl}-(2,2-dimethylpropyl)amine | 444 |
| 21 | {6-[5-(2,4-Difluorophenyl)-2-(2,6-difluorophenyl)-3H-imidazol-4-yl]-3-nitropyridin-2-yl}-(2,2-dimethylpropyl)amine | 500 |

Preparation 22

6-[2-(2,6-Dichlorophenyl)-5-phenyl-1H-imidazol-4-yl]-$N^2$-isobutylpyridine-2,3-diamine Add sodium dithionite (2.58 g, 14.82 mmol) followed by 32% $NH_4OH$ (9 mL) to a solution of {6-[2-(2,6-dichlorophenyl)-5-phenyl-1H-imidazol-4-yl]-3-nitropyridin-2-yl}isobutylamine (1.43 g, 2.96 mmol) in 50 mL of 1:1 THF:water mixture. Stir the mixture at RT for 2 h. Dilute with EtOAc. Wash the organic layer with saturated aqueous NaCl and dry the organic phase over $Na_2SO_4$. Concentrate to yield the title compound (1.32 g, 98%).

Preparation 23

2-Isobutylamino-3-nitro-6-[3-(4-fluorophenyl)-1-morpholinoethylpyrazol-4-yl]pyridine 2-Isobutylamino-3-nitro-6-(4-fluorophenylethanone) pyridine Add an aqueous suspension of HgO (0.55 g, 2.54 mmol) in 100 mL of 4% $H_2SO_4$ to a solution of 2-isobutylamino-3-nitro-6-(4-fluorophenyl)ethynylpyridine (3.99 g, 12.7 mmol) in 100 mL of MeOH. Stir at 95° C. for 17 h and cool to RT. Filter the mixture through a filtering agent and dissolve the precipitate with EtOAc (5×100 mL). Concentrate and wash the residue with 10:2:1 hexane:diethyl ether:MeOH (130 mL) to provide the title compound (2.60 g, 62%).

MS (ES): m/z=332 [M+H].

2-Isobutylamino-3-nitro-6-[3-(4-fluorophenyl)pyrazol-4-yl]pyridine

Add dimethylformamide dimethyl acetal (4.50 mL, 33.8 mmol) to a stirred solution of 2-isobutylamino-3-nitro-6-(4-fluorophenyl-ethanone)-pyridine (5.63 g, 16.1 mmol) in 15 mL of dry DMF. Heat the mixture at 80° C. for 6 h, cool to RT and concentrate. Dissolve the residue in 100 mL of EtOH, add 8.30 mL of hydrazine (80% in $H_2O$), stir for 2 h and concentrate. Purify the residue (silica gel chromatography, eluting with hexanes:EtOAc 1:1) to give the title compound (4.51 g, 75%).

MS (ES): m/z=356 [M+H].

2-Isobutylamino-3-nitro-6-[3-(4-fluorophenyl)-1-morpholinoethylpyrazol-4-yl]pyridine Treat a solution of 2-isobutylamino-3-nitro-6-[3-(4-fluorophenyl)pyrazol-4-yl]pyridine (1.25 g, 3.52 mmol) in dry DMF (15 mL) with 95% NaH (0.36 g, 14.3 mmol) at 0° C. for 15 min. Add morpholinoethylchloride hydrochloride (0.983 g, 5.28 mmol) and slowly warm to RT. Add additional NaH (0.36 g, 14.3 mmol), after 1 h and stir the reaction mixture for 24 h. Quench with MeOH (1 mL) and dilute with water (30 mL). Extract with EtOAc (100 mL), dry with $MgSO_4$, and concentrate. Purify the residue (silica gel chromatography, eluting with hexanes:EtOAc 1:2) to give the title compound (1.35 g, 81%).

MS (ES): m/z=469 [M+H].

Preparation 24

(2,2-Dimethylpropyl)-[3-nitro-6-(5-phenyl-3H-[1,2,3]triazol-4-yl)-pyridin-2-yl]amine Add sodium azide (0.065 g) to a solution of 2,2-dimethylpropyl-(2-nitro-5-phenylethynylphenyl)amine (0.153 g) in of DMSO (2.5 mL). Heat at 80° C. for 2 h. Cool to RT. Add 10 mL of 1N HCl and extract with EtOAc (20 mL) and wash with saturated aqueous NaCl (2×10 mL). Dry the remaining organic phase over $Na_2SO_4$ and concentrate. Purify the residue (silica gel chromatography, eluting with EtOAc:hexanes 1:2) to give the title compound as yellow solid (0.176 g, 100%).

MS (ES): m/z=353 [M+H].

Preparation 25

2-Amino-5-(2-oxo-2-phenylacetyl)imidazo[4,5-b]pyridine-3-sulfonic acid dimethylamide

N,N-dimethyl-N'-(6-chloro-3-nitropyridin-2-yl)sulfonic acid

Stir a mixture of 2,6-dichloro-3-nitropyridine (1 g, 2.60 mmol) and N,N-dimethylsulfamide (0.78 g, 3.12 mmol) in dry DMF (5 mL). Add lithium hydride (0.11 g, 6.76 mmol) and stir at RT overnight. Add 10 mL of water and 3N HCl until pH=7. Filter the yellow solid to provide the title compound (85%).

MS (ES): m/z=279 [M+H].

N,N-dimethyl-N'-(3-nitro-6-phenylethynylpyridin-2-yl)sulfonic acid

Bubble nitrogen through a mixture of N,N-dimethyl-N'-(6-chloro-3-nitropyridin-2-yl)sulfonic acid (3.86 g, 13.7 mmol), phenylacetylene (2.3 mL, 20.67 mmol), triphenylphosphine (0.09 g, 0.68 mmol) and copper (I) iodide (0.06 g, 0.34 mmol) in triethylamine (30 mL) and THF (60 mL) for 3 min. Add bis(triphenylphosphine)palladium (II) chloride (0.24 g, 0.34 mmol) to the mixture and heat at 110° C. for 4 h. Filter through a pad of filtering agent and concentrate. Purify the residue (silica gel chromatography, eluting with 1:1 hexanes:EtOAc) to give the title compound (80%).

MS (ES): m/z=346 [M+H].

N,N-dimethyl-N'-(3-amino-6-phenylethynylpyridin-2-yl)sulfonic acid

Stir a mixture of N,N-dimethyl-N'-(3-nitro-6-phenylethynylpyridin-2-yl)sulfonic acid (0.09 g, 0.26 mmol) and tin chloride dihydrate (0.35 g, 1.56 mmol) in EtOAc (5 mL) and EtOH (2.5 mL) at 70° C. for 2 h. Concentrate and purify the residue (silica gel chromatography, eluting with 1:1 hexanes:EtOAc) to give the title compound (65%).

MS (ES): m/z=317 [M+H].

2-Amino-5-phenylethynylimidazo[4,5-b]pyridine-3-sulfonic acid dimethylamide Stir a mixture of N,N-dimethyl-N'-(3-amino-6-phenylethynylpyridin-2-yl)sulfonic acid (0.20 g, 0.63 mmol), cyanogen bromide (0.07 g, 0.69 mmol) and lithium methoxide (0.04 g, 0.94 mmol) in 1,2 dichloroethane (20 mL) at 80° C. overnight. Concentrate and purify the residue (silica gel chromatography, eluting with 1:1 hexanes:EtOAc) to give the title compound (45%).

MS (ES): m/z=342 [M+H].

2-Amino-5-(2-oxo-2-phenylacetyl)imidazo[4,5-b]pyridine-3-sulfonic acid dimethylamide Add a solution of 2-amino-5-phenylethynylimidazo[4,5-b]pyridine-3-sulfonic acid dimethylamide (0.10 g, 0.31 mmol) in acetone (4 mL) over a mechanically stirred solution of NaHCO$_3$ (0.01 g, 0.15 mmol) and MgSO$_4$ (0.07 g, 0.62 mmol) in water (4 mL) at 0° C.

Add KMnO$_4$ (0.12 g, 0.748 mmol) and stir at 0° C. overnight. Add Na$_2$SO$_3$ (0.13 g), and stir for 1 h. Add EtOAc and wash with a saturated aqueous solution of NaCl, and concentrate to give the title compound as an orange solid which is used without further purification (68% yield).

MS (ES): m/z=372 [M+H].

Preparation 26

Propane-2-sulfonic acid {3-amino-6-[2-(2,6-difluorophenyl)-5-phenyl-3H-imidazol-4-yl]pyridin-2-yl}amide

Propane-2-sulfonic acid (3-nitro-6-phenylethynylpyridin-2-yl)amide

Add propane-2-sulfonic acid (5-chloro-2-nitrophenyl)amide (10 g, 35.7 mmol), phenylacetylene (5.9 mL, 53.6 mmol) and triphenylphosphine (0.46 g, 1.78 mmol) to a solution of triethylamine (25 mL, 178.5 mmol) in dry THF (25 mL) and flush the system with nitrogen. Add dichlorobis(triphenylphosphine)palladium(1) (0.625 g, 0.89 mmol) and copper (I) iodide (0.17 g, 0.89 mmol) to this stirring mixture. Heat the reaction to reflux for 4 h. Cool to RT and concentrate to a slurry. Filter the crude material through a plug of silica gel using EtOAc as the eluting solvent. Concentrate the filtrate and crystallize the title compound from EtOAc-hexanes (7.9 g, 64%).

MS (ES): m/z=346 [M+H].

Propane-2-sulfonic acid [3-nitro-6-(2-oxo-2-phenylacetyl)pyridin-2-yl]amide Heat a mixture of propane-2-sulfonic acid (3-nitro-6-phenylethynylpyridin-2-yl)amide (1.8 g, 5.26 mmol) and palladium (II) chloride (0.93 g, 0.53 mmol) in dry DMSO (20 mL) at 120° C. for 12 h under a nitrogen atmosphere. Cool to RT, concentrate to a slurry, and purify (silica gel chromatography, eluting with a gradient of 20:80 EtOAc:hexanes to 30:70 EtOAc:hexanes) to give the title compound (1.07 g, 54%).

MS (ES): m/z=346 [M+H].

Propane-2-sulfonic acid {6-[2-(2,6-difluorophenyl)-5-phenyl-3H-imidazol-4-yl]-3-nitropyridin-2-yl}amide Heat a mixture of propane-2-sulfonic acid [3-nitro-6-(2-oxo-2-phenylacetyl)pyridin-2-yl]amide (0.25 g, 0.67 mmol), 2,6-difluorobenzaldehyde (0.146 mL, 1.35 mmol) and ammonium acetate (0.78 g, 10.05 mmol) in AcOH (5 mL) at 110° C. for 2 h. Cool to RT and concentrate. Dilute with EtOAc (30 mL), extract successively with saturated NaHCO$_3$ and saturated aqueous NaCl. Dry the organic layer over NaSO$_4$, concentrate, and purify (silica gel chromatography, eluting with 30:70 EtOAc:hexanes) to give the title compound (0.32 g, 95%).

MS (ES): m/z=500 [M+H].

Propane-2-sulfonic acid {3-amino-6-[2-(2,6-difluorophenyl)-5-phenyl-3H-imidazol-4-yl]-pyridin-2-yl}amide Add 10% Pd/C (0.033 g) to a stirring solution of propane-2-sulfonic acid {6-[2-(2,6-difluorophenyl)-5-phenyl-3H-imidazol-4-yl]-3-nitropyridin-2-yl}amide (0.33 g, 0.66 mmol) in MeOH (10 mL). Add sodium borohydride (0.124 g, 3.3 mmol) in portions and with stirring under nitrogen for 15 min. Filter the catalyst and concentrate. Dilute with EtOAc (20 mL) and extract successively with saturated NaHCO$_3$ and saturated aqueous NaCl. Dry the organic layer over Na$_2$SO$_4$ and concentrate to give the title compound (0.3 g, 98%).

MS (ES): m/z=470 [M+H].

Preparation 27

Propane-2-sulfonic acid {3-amino-6-[2-(2,6-dichlorophenyl)-5-phenyl-3H-imidazol-4-yl]-pyridin-2-yl}amide Heat a mixture of propane-2-sulfonic acid {6-[2-(2,6-dichlorophenyl)-5-phenyl-3H-imidazol-4-yl]-3-nitropyridin-2-yl}amide (0.262 g, 0.49 mmol) and tin (II) chloride dihydrate (0.55 g, 2.46 mmol) in EtOH (10 mL) at 100° C. for 1 h. Cool to RT and concentrate to a slurry. Pour the reaction mixture into saturated $NaHCO_3$ (20 mL) and add a filtering agent. Filter and wash with EtOAc. Separate the layers and extract successively with saturated $NaHCO_3$ and saturated aqueous NaCl. Dry the organic layer over $Na_2SO_4$ and concentrate to give the title compound (0.21 g, 85%).

MS (ES): m/z=504 [M+H].

Preparation 28

1-Benzyl-2-methyl-4-bromo-5-(2,4-difluorophenyl)-1H-imidazole

1-Benzyl-2-methyl-5-bromo-1H-imidazole

Add N-bromosuccinimide (7.85 g, 44 mmol) to a solution of 1-benzyl-2-methyl-1H-imidazole (8.0 g, 46 mmol) in chloroform (200 mL) and stir for 6 h. Wash with saturated aqueous sodium hydrogen carbonate and saturated aqueous NaCl, dry over $MgSO_4$, and filter through a pad of silica gel. Concentrate filtrate and suspend the residue in diethyl ether (600 mL), heat to reflux, and filter hot. Concentrate ether filtrate to give the title compound as a tan solid (9.3 g).

MS (ES): m/z=252 [M+H].

1-Benzyl-2-methyl-5-(2,4-difluorophenyl)-1H-imidazole

Heat a mixture of 1-benzyl-2-methyl-5-bromo-1H-imidazole (4.71 g, 18.7 mmol), 2,4-difluorophenyl boronic acid (6.92 g, 43.8 mmol), bis(acetato)bis(triphenylphosphine)-palladium(II) (1.4 g, 1.875 mmol), 2N $Na_2CO_3$ (19 mL, 38 mmol), MeOH (19 mL) and 1,2-dimethoxyethane (120 mL) to reflux for 18 h. Cool to RT. Add water and EtOAc and separate the layers. Dry organic layer over $MgSO_4$, filter, and concentrate. Purify the residue (silica gel chromatography, eluting with $EtOAc:CH_2Cl_2$ mixtures) to give the desired compound (3.59 g).

MS (ES): m/z=285 [M+H].

Bromination

Stir a mixture of 1-benzyl-2-methyl-5-(2,4-difluorophenyl)-1H-imidazole (3.58 g, 12.6 mmol) and N-bromosuccinimide (2.24 g, 12.6 mmol) in chloroform (100 mL) at RT for 18 h. Add the reaction mixture directly onto silica gel and elute with $CH_2Cl_2$:EtOAc mixtures to give title compound (3.41 g).

MS (ES): m/z=364 [M+H].

Preparation 29

2-tert-Butyl-4-(4-fluorophenyl)oxazole

Reflux a solution of commercially available 2-bromo-4'-fluoroacetophenone (100.00 g, 460 mmol), 2,2-dimethylpropionamide (93.06 g, 20 mmol) in 1,4-dioxane (600 mL) for 2 days. Filter precipitate, concentrate filtrate, and purify (silica gel chromatography, eluting with hexanes:EtOAc 60:1) to give the title compound (55 g, 55%).

MS (ES): m/z=220 [M+H].

The compounds of Preparations 30-31 may be prepared essentially as described in Preparation 29.

| Prep. | Compound | MS (ES): m/z [M + H] |
|---|---|---|
| 30 | 2-tert-Butyl-4-(2,4-difluorophenyl)oxazole | 238 |
| 31 | 4-(4-Fluorophenyl)-2-isopropyloxazole | 206 |

Preparation 32

2-tert-Butyl-4-(4-fluorophenyl)-5-trimethylstannanyloxazole

Dissolve 2-tert-butyl-4-(4-fluorophenyl)oxazole (0.61 g, 2.77 mmol) in THF (15 ml) and add tert-butyl lithium (3.3 ml, 1.7 M) at −78° C. Stir the mixture for 45 min. Add trimethylstannanyl chloride (0.58 g, 2.90 mmol) and allow the temperature to reach RT. Stir for 2 h and add an ammonium chloride solution (200 μL, pH=8 with ammonia) and concentrate.

$^1$H NMR ($CDCl_3$) δ 7.46 (m. 2H), 6.95 (m, 2H), 1.32 (s, 9H), 0.24 (s, 9H).

Preparation 33

4-(4-Fluorophenyl)-2-methylthiazole

Reflux a solution of 2-bromo-4'-fluoroacetophenone (10 g, 46 mmol) and thioacetamide (6.9 g, 92 mmol) in 1,4-dioxane (60 mL) for 3 h. Filter the precipitate and wash with EtOAc to give the title compound (6.5 g, 73%).

MS (ES): m/z=194 [M+H].

The compound of Preparation 34 may be prepared essentially as described in Preparation 33.

| Prep. | Compound | MS (ES): m/z [M + H] |
|---|---|---|
| 34 | 2-Methyl-4-phenylthiazole | 176 |

Preparation 35

2-Amino-5-bromoimidazo[4,5-b]pyridine-3-sulfonic acid dimethylamide 2,6-Dibromo-3-nitropyridine Heat at 50° C. a mixture of 2,6-dichloro-3-nitropyridine (9 g) and hydrobromic acid (90 mL) in AcOH (30%) overnight. Cool to RT and pour into water (600 mL). Filter the solid to provide the title compound (87%).

$^1$H NMR ($CDCl_3$) δ 7.93 (d, J=8.14 Hz, 1H), 7.55 (d, J=8.14 Hz, 1H).

N,N-Dimethyl-N'-(6-bromo-3-nitropyridin-2-yl)sulfonic acid

Stir a mixture of 2,6-dibromo-3-nitropyridine (11.3 g, 39.25 mmol) and N,N-dimethylsulfamide (0.006 g, 47.10 mmol) in DMF (40 mL). Add lithium hydride (0.81 g, 102.05 mmol) and stir at RT overnight. Add 100 mL of water and 3 N HCl until pH=7. Filter the yellow solid to provide the title compound (93%).

$^1$H NMR (DMSO-d$_6$) δ 10.25 (br s, 1H), 8.41 (d, J=8.59 Hz, 1H), 7.50 (d, J=8.59 Hz, 1H), 2.95 (2, 6H).

N,N-dimethyl-N'-(3-amino-6-bromo-pyridin-2-yl)-sulfonic acid

Heat a mixture of N,N-dimethyl-N'-(6-bromo-3-nitropyridin-2-yl)sulfonic acid (11.6 g, 35.69 mmol) and tin chloride (40 g, 178 mmol) in EtOAC:EtOH 500:250 mL for 4 h. Concentrate and purify the residue (silica gel chromatography, eluting with 1:1 hexane:EtOAc). Triturate with water to provide the title compound (85%).

MS (ES): m/z=297 [M+H].

2-Amino-5-bromoimidazo[4,5-b]pyridine-3-sulfonic acid dimethylamide

Stir a mixture of N,N-dimethyl-N'-(3-amino-6-bromopyridin-2-yl)sulfonic acid (0.40 g, 1.35 mmol), cyanogen bromide (0.08 g, 1.48 mmol) and lithium methoxide (0.08 g, 2.02 mmol) in 1,2-dichloroethane (400 mL). Stir at 80° C. for 2 h. Concentrate and purify the residue (silica gel chromatography, eluting with 1:1 hexane:EtOAc) to give the title compound (82%).

MS (ES): m/z=322 [M+H].

Preparation 36

1-[2-amino-3-(2,2-dimethyl-propyl)-3H-imidazo[4,5-b]pyridin-5-yl]-2-(2,4-difluoro-phenyl)-ethane-1,2-dione

5-(2,4-difluoro-phenylethynyl)-3-(2,2-dimethyl-propyl)-3H-imidazo[4,5-b]pyridin-2-ylamine Combine 5-bromo-3-(2,2-dimethyl-propyl)-3H-imidazo[4,5-b]pyridin-2-ylamine (30.00 g, 105.94 mmol), Et$_3$N (60 mL), and Pd(OAc)$_2$[P(Ph)$_3$]$_2$ (3.97 g, 5.30 mmol) in toluene (150 mL) and heat the resulting mixture to ~65° C. under nitrogen. Add 1-ethynyl-2,4-difluoro-benzene (21.95 g, 158.92 mmol) in toluene (30 mL) dropwise to the above mixture, and then heat the resulting reaction mixture at 80° C. for 3 h. Cool the reaction to 25° C. and quench with saturated aqueous NH$_4$Cl (300 mL). Stir the resulting reaction mixture at room temperature for 20 minutes, then filter, washing the solid with H$_2$O and drying under vacuum filtration for 30 minutes. Slurry the solid in MTBE (200 mL), then filter and rinse with MTBE (50 mL). Dry the recovered solid under vacuum filtration to provide 14.47 g of the title compound as a light-yellow solid.

MS(ES+): m/z=341 (M+1)

Oxidation

Treat a solution of 5-(2,4-difluoro-phenylethynyl)-3-(2,2-dimethyl-propyl)-3H-imidazo[4,5-b]pyridin-2-ylamine (14.47 g, 42.51 mmol) in acetone (350 mL) with a solution of MgSO$_4$ (10.23 g, 85.00 mmol) and NaHCO$_3$ (1.79 g, 21.30 mmol) in water (200 mL). Place the resulting reaction mixture in a H$_2$O bath. Add celite (28.50 g), followed by KMnO$_4$ (14.11 g, 89.28 mmol) over 10 minutes, as the reaction exotherms to ~30° C. Stir at room temperature for 3 h, then quench with 10 wt % of aqueous Na$_2$SO$_3$ (150 mL). Stir for 30 minutes, then filter over a pad of celite, washing with 10% MeOH/EtOAc (2×700 mL each). Separate the layers of the filtrate and extract the aqueous with EtOAc (2×500 mL each). Wash the combined organics with H$_2$O (500 mL) and saturated aqueous sodium chloride (500 mL), then dry over Na$_2$SO$_4$, filter, and concentrate under reduced pressure to afford a solid. Wash the filter pad of celite with 10% MeOH/EtOAc and concentrate the filtrate under reduced pressure to obtain additional solid. Combine the solids and purify by column chromatography, eluting with 2% of 2N NH$_4$/MeOH in EtOAc, then 5% of 2N NH$_4$/MeOH in EtOAc to give 13.08 g (82% yield) of the title compound as an orange-brown solid.

MS (ES+): m/z=373 (M+1)

Preparation 37

{6-[2-tert-Butyl-5-(4-fluoro-phenyl)-3H-imidazol-4-yl]-3-nitro-pyridin-2-yl}-(1(R),2,2-trimethyl-propyl)-amine

1-[6-(1(R),2,2-trimethylpropylamino)-5-nitropyridin-2-yl]-2-((4-fluorophenyl)ethane-1,2-dione Dissolve [6-(4-fluoro-phenylethynyl)-3-nitro-pyridin-2-yl]-(1(R),2,2-trimethyl-propyl)-amine (2.73 g, 8.00 mmol) in acetone (60 mL). Add water (20 mL), then NaHCO$_3$ (336 mg, 4 mmol, 0.5 equiv), and MgSO$_4$ (1.9 g, 16 mmol, 2.0 equiv) and chill the reaction to about 3° C. Add KMnO$_4$ (2.5 g, 16 mmol, 2.0 equiv) portionwise with vigorous stirring while maintaining the temperature below 3° C. Quench the reaction after 1-2 h by adding water (20 mL) and Na$_2$SO$_3$ (4.5 g, 36 mmol) and stirring the mixture at ambient temperature for 1 h. Filter the suspension over Celite® with the aid of 600 mL ethyl acetate and about 300 mL water. Separate the layers and wash the organic layer four times with saturated aqueous NaHCO$_3$ and twice with saturated aqueous NaCl. Dry the organic layer with Na$_2$SO$_4$, filter off the solids, and concentrate the supernatant under reduced pressure. Subject the residue to medium pressure silica gel chromatography eluting with a 50-70% gradient of CH$_2$Cl$_2$ in hexanes to give the desired compound as an orange oil (1.82 g, 61% yield).

MS (ESI): m/z=374.1 (M+H)$^+$.

Ring Formation

Dissolve 1-[6-(1(R),2,2-trimethylpropylamino)-5-nitropyridin-2-yl]-2-((4-fluorophenyl)ethane-1,2-dione (747 mg, 2.0 mmol) in glacial acetic acid (10 mL), add ammonium acetate (2.3 g, 30 mmol, 15 equiv), and then add trimethylacetaldehyde (344 mg, 4.0 mmol, 2 equiv). Heat the reaction mixture to 100° C. for 1 h and concentrate under reduced pressure. Partition the resulting solids between ethyl acetate and water. Wash the organic layer 5 times with saturated aqueous NaHCO$_3$, and twice with saturated aqueous NaCl. Dry the organic layer with Na$_2$SO$_4$, filter, and concentrate under reduced pressure. Subject the residue to medium pressure silica gel chromatography eluting with an isocratic 10% ethyl acetate/hexanes system to give the title compound as an orange solid. (589 mg, 67% yield)

MS (ESI): m/z=440.2 (M+H)$^+$

The compounds of Preparations 38-40 may be prepared essentially as described in Preparation 37.

| Prep. | Compound | MS (ESI): m/z [M + H] |
|---|---|---|
| 38 | {6-[2-(2,6-difluorophenyl)-5-(4-fluoro-phenyl)-3H-imidazol-4-yl]-3-nitro-pyridin-2-yl}-(1(R),2,2-trimethyl-propyl)-amine | 496.1 |
| 39 | {6-[2-(2-fluoro-6-trifluoromethylphenyl)-5-(4-fluoro-phenyl)-3H-imidazol-4-yl]-3-nitro-pyridin-2-yl}-(1(R),2,2-trimethyl-propyl)-amine | 546.2 |
| 40 | {6-[2-(2-chloro-6-fluorophenyl)-5-(4-fluoro-phenyl)-3H-imidazol-4-yl]-3-nitro-pyridin-2-yl}-(1(R),2,2-trimethyl-propyl)-amine | 512.2 |

Preparation 41

{6-[2-tert-Butyl-5-(4-fluoro-phenyl)-3H-imidazol-4-yl]-3-nitro-pyridin-2-yl}-(2,2-dimethyl-propyl)-amine Dissolve 1-(4-fluoro-phenyl)-2-[5-nitro-6-(2,2-dimethyl-propylamino)-pyridin-2-yl]-ethane-1,2-dione (1.08 g, 3.0 mmol) in glacial acetic acid, add ammonium acetate (3.47 g, 45 mmol, 15 equiv), and then add trimethylacetaldehyde (517 mg, 6.0 mmol, 2 equiv). Heat the reaction mixture to 100° C. for 1 h and concentrate under reduced pressure. Partition the resulting solids between ethyl acetate and water. Add NaHCO$_3$ until gas evolution ceases. Wash the organic layer 5 times with saturated aqueous NaHCO$_3$ and once with saturated aqueous NaCl. Dry the organic layer with Na$_2$SO$_4$, filter, and concentrate under reduced pressure to give the title compound as a yellow-orange solid. (1.25 g, 97% yield)

Exact MS: calc.: in m/z=426.230 (M+H)$^+$; found: m/z=426.2313 (M+H)$^+$.

EXAMPLE 1

5-(2-tert-Butyl-5-phenyl-3H-imidazol-4-yl)-3-(2,2-dimethylpropyl)-3H-imidazo[4,5-b]pyridin-2-ylamine methanesulfonate Stir a suspension of 6-(2-tert-butyl-5-phenyl-3H-imidazol-4-yl)-3-nitropyridin-2-yl]-(2,2-dimethylpropyl)amine (0.20 g, 0.5 mmol) and 10% palladium on carbon (0.025 g) in EtOH (10 mL) under a balloon of hydrogen overnight. Filter the suspension through a filtering agent and wash with EtOH (2×5 mL). Concentrate the filtrate to about 5 mL, and treat at RT with cyanogen bromide (1.3 mmol). Quench with saturated aqueous sodium bicarbonate (2 mL) and stir for 15-60 min. Dilute the mixture with water (5 mL) and extract with CH$_2$Cl$_2$ (2×10 mL). Wash the combined organic phases with saturated aqueous NaCl (5 mL), dry with MgSO$_4$, filter, concentrate, and purify (silica gel chromatography, eluting with a step gradient beginning with 100% CH$_2$Cl$_2$, to 5:95 ammoniated MeOH:CH$_2$Cl$_2$) to give the desired compound. The free base is isolated and then converted to the methanesulfonate salt by treatment of a MeOH-water solution with methanesulfonic acid followed by lyophilization to give the title compound.

MS (ES): m/z=402 [M+H].

The compounds of EXAMPLES 2-14 may be prepared essentially as described in EXAMPLE 1.

| EXAMPLE | Compound | MS (ES): m/z [M + H] |
|---|---|---|
| 2 | 5-[2-(2,6-Difluorophenyl)-5-phenyl-3H-imidazol-4-yl]-3-(2,2-dimethylpropyl)-3H-imidazo[4,5-b]pyridin-2-ylamine methanesulfonate | 459 |
| 3 | 5-(2-tert-Butyl-5-phenyl-3H-imidazol-4-yl)-3-cyclopropylmethyl-3H-imidazo[4,5-b]pyridin-2-ylamine methanesulfonate | 387 |
| 4 | 5-(2-Cyclopropyl-5-phenyl-3H-imidazol-4-yl)-3-(2,2-dimethylpropyl)-3H-imidazo[4,5-b]pyridin-2-ylamine methanesulfonate | 387 |
| 5 | 3-(2,2-Dimethylpropyl)-5-[5-(4-fluorophenyl)-2-(2-fluoro-6-trifluoromethylphenyl)-3H-imidazol-4-yl]-3H-imidazo[4,5-b]pyridin-2-ylamine methanesulfonate | 527 |
| 6 | 3-(2,2-Dimethylpropyl)-5-[2-(2-fluoro-6-trifluoromethylphenyl)-5-phenyl-3H-imidazol-4-yl]-3H-imidazo[4,5-b]pyridin-2-ylamine methanesulfonate | 509 |
| 7 | 5-[2-Cyclopropyl-5-(4-fluorophenyl)-3H-imidazol-4-yl]-3-(2,2-dimethylpropyl)-3H-imidazo[4,5-b]pyridin-2-ylamine methanesulfonate | 405 |
| 8 | 5-[2-(2,6-Difluorophenyl)-5-(4-fluorophenyl)-3H-imidazol-4-yl]-3-(2,2-dimethylpropyl)-3H-imidazo[4,5-b]pyridin-2-ylamine methanesulfonate | 477 |
| 9 | 5-[2-tert-Butyl-5-(4-fluorophenyl)-3H-imidazol-4-yl]-3-(2,2-dimethylpropyl)-3H-imidazo[4,5-b]pyridin-2-ylamine methanesulfonate | 421 |
| 10 | 5-[2-tert-Butyl-5-(4-fluorophenyl)-3H-imidazol-4-yl]-3-cyclopropylmethyl-3H-imidazo[4,5-b]pyridin-2-ylamine methanesulfonate | 405 |
| 11 | 5-[2-tert-Butyl-5-(2,4-difluorophenyl)-3H-imidazol-4-yl]-3-(2,2-dimethylpropyl)-3H-imidazo[4,5-b]pyridin-2-ylamine methanesulfonate | 439 |
| 12 | R-5-[2-tert-Butyl-5-(4-fluorophenyl)-3H-imidazol-4-yl]-3-(1,2,2-trimethylpropyl)-3H-imidazo[4,5-b]pyridin-2-ylamine methanesulfonate | 435 |

-continued

| EXAMPLE | Compound | MS (ES): m/z [M + H] |
|---|---|---|
| 13 | R-5-[2-(2,6-Difluorophenyl)-5-(4-fluorophenyl)-3H-imidazol-4-yl]-3-(1,2,2-trimethylpropyl)-3H-imidazo[4,5-b]pyridin-2-ylamine methanesulfonate | 491 |
| 14 | R-5-[5-(4-Fluorophenyl)-2-(2-fluoro-6-trifluoromethyl-phenyl)-3H-imidazol-4-yl]-3-(1,2,2-trimethylpropyl)-3H-imidazo[4,5-b]pyridin-2-ylamine methanesulfonate | 541 |

EXAMPLE 15

3-Cyclopropylmethyl-5-[2-(2,6-dichlorophenyl)-5-(4-fluorophenyl)-3H-imidazol-4-yl]-3H-imidazo[4,5-b]pyridin-2-ylamine methanesulfonate Treat a suspension of (cyclopropylmethyl{6-[2-(2,6-dichlorophenyl)-5-(4-fluorophenyl)-3H-imidazol-4-yl]-3-nitropyridin-2-yl}amine (0.250 g, 0.5 mmol) in EtOH (10 mL) with tin dichloride dihydrate (0.5641 g, 2.5 mmol) and heat at reflux for 2.5 h under nitrogen. Cool to RT and quench slowly with saturated aqueous $NaHCO_3$ (5 mL) and EtOAc (5 mL). Add filtering agent to the resulting suspension and dilute the mixture further with 5 mL each of aqueous $NaHCO_3$ and EtOAc. Filter the mixture through a pad of the filtering agent. Wash the solid with 10 mL each of aqueous $NaHCO_3$ and EtOAc. Separate the layers and extract the aqueous phase with EtOAc (10 mL). Wash the combined organic phases with saturated aqueous NaCl (5 mL), dry with $MgSO_4$, filter and concentrate. Dissolve the crude phenylenediamine in EtOH (5 mL) and treat with cyanogen bromide (1.0 mmol). Quench with saturated aqueous $NaHCO_3$ (2 mL) and stir for 15-60 min. Dilute mixture with water (5 mL) and extract with $CH_2Cl_2$ (2×10 mL). Wash the combined organic phases with saturated aqueous NaCl (5 mL), dry with $MgSO_4$, filter, concentrate, and purify (silica gel chromatography, eluting with a step gradient beginning with 100% $CH_2CO_2$ to 5:95 5% ammonia in MeOH:$CH_2Cl_2$ to give the desired compound. Isolate the free base and convert it to the methanesulfonate salt by treatment of a MeOH-water solution with methanesulfonic acid followed by lyophilization.

MS (ES): nm/z=495.1 [M+H].

The compounds of EXAMPLES 16-35 may be prepared essentially as described in EXAMPLE 15.

| EXAMPLE | Compound | MS (ES): m/z [M + H]) |
|---|---|---|
| 16 | 3-Cyclopropylmethyl-5-[2-(2,6-difluorophenyl)-5-(4-fluorophenyl)-3H-imidazol-4-yl]-3H-imidazo[4,5-b]pyridin-2-ylamine methanesulfonate | 461 |
| 17 | 5-[2-(2,6-Dichlorophenyl)-5-(4-fluorophenyl)-3H-imidazol-4-yl]-3-(2,2-dimethylpropyl)-3H-imidazo[4,5-b]pyridin-2-ylamine methanesulfonate | 509 |
| 18 | 5-[2-(2-Chloro-6-fluorophenyl)-5-phenyl-3H-imidazol-4-yl]-3-(2,2-dimethylpropyl)-3H-imidazo[4,5-b]pyridin-2-ylamine methanesulfonate | 475 |
| 19 | 3-Cyclopropylmethyl-5-[2-(2,6-difluorophenyl)-5-phenyl-3H-imidazol-4-yl]-3H-imidazo[4,5-b]pyridin-2-ylamine methanesulfonate | 443 |
| 20 | 3-Cyclopropylmethyl-5-[2-(2,6-dichlorophenyl)-5-phenyl-3H-imidazol-4-yl]-3H-imidazo[4,5-b]pyridin-2-ylamine methanesulfonate | 476 |
| 21 | 5-[5-(2,4-Difluorophenyl)-2-(2,6-difluorophenyl)-3H-imidazol-4-yl]-3-(2,2-dimethylpropyl)-3H-imidazo[4,5-b]pyridin-2-ylamine methanesulfonate | 495 |
| 22 | 5-[3-(4-Fluorophenyl)-1-methylpyrazol-4-yl]-3H-3-isobutyl-imidazo[4,5-b]pyridin-2-ylamine methanesulfonate | 365 |
| 23 | 5-[5-(4-Fluorophenyl)-1-methylpyrazol-4-yl]-3H-3-isobutyl-imidazo[4,5-b]pyridin-2-ylamine methanesulfonate | 365 |
| 24 | 5-[3-(4-Fluorophenyl)-1-morpholinoethylpyrazol-4-yl]-3H-3-isobutyl-imidazo[4,5-b]pyridin-2-ylamine-methanesulfonate | 464 |
| 25 | 5-[3-(4-Fluorophenyl)-pyrazol-4-yl]-3H-3-isobutyl-imidazo[4,5-b]pyridin-2-ylamine di-methanesulfonate | 351 |
| 26 | 3H-3-isobutyl-5-(3-phenyl-1-isopropylpyrazol-4-yl)-imidazo[4,5-b]pyridin-2-ylamine di-methanesulfonate | 375 |
| 27 | 3H-3-isobutyl-5-(3-phenyl-1-methylpyrazol-4-yl)-imidazo[4,5-b]pyridin-2-ylamine di-methanesulfonate | 347 |
| 28 | 3H-3-isobutyl-5-(3-phenyl-pyrazol-4-yl)-imidazo[4,5-b]pyridin-2-ylamine di-methanesulfonate | 333 |
| 29 | 5-[3-(2,4-Difluorophenyl)pyrazol-4-yl]-3H-3-isobutyl-imidazo[4,5-b]pyridin-2-ylamine di-methanesulfonate | 369 |

| EXAMPLE | Compound | MS (ES): m/z [M + H]) |
|---|---|---|
| 30 | 5-[2-(2,6-Difluorophenyl)-5-phenyl-3H-imidazol-4-yl]-3-isobutyl-3H-imidazo[4,5-b]pyridin-2-ylamine methanesulfonate | 445 |
| 31 | 5-[2-(2,6-Dichlorophenyl)-5-phenyl-3H-imidazol-4-yl]-3-(2,2-dimethylpropyl)-3H-imidazo[4,5-b]pyridin-2-ylamine methanesulfonate | 491 |
| 32 | 5-[2-(2,6-Dichlorophenyl)-5-phenyl-1H-imidazol-4-yl]-3-isobutyl-3H-imidazo[4,5-b]pyridin-2-ylamine methanesulfonate | 477 |
| 33 | 5-[2-(2,6-Dichlorophenyl)-5-(4-fluorophenyl)-1H-imidazol-4-yl]-3-isobutyl-3H-imidazo[4,5-b]pyridin-2-ylamine methanesulfonate | 495 |
| 34 | 5-[2-(2,6-Dichlorophenyl)-5-(2,4-difluorophenyl)-1H-imidazol-4-yl]-3-isobutyl-3H-imidazo[4,5-b]pyridin-2-ylamine methanesulfonate | 513 |
| 35 | R-5-[2-(2-Chloro-6-fluorophenyl)-5-(4-fluorophenyl)-3H-imidazol-4-yl]-3-(1,2,2-trimethylpropyl)-3H-imidazo[4,5-b]pyridin-2-ylamine methanesulfonate | 507 |

EXAMPLE 36

5-[2-tert-Butyl-5-(4-fluorophenyl)-3H-imidazol-4-yl]-3-(2,2-dimethylpropyl)-2-methyl-3H-imidazo[4,5-b]pyridine methanesulfonate Reduce and isolate {6-[2-tert-butyl-5-(4-fluorophenyl)-3H-imidazol-4-yl]-3-nitropyridin-2-yl}-(2,2-dimethylpropyl)amine (0.43 g; 1.0 mmol) as in EXAMPLE 1. React the crude diamine with neat triethylorthoacetate at 120° C. overnight. Concentrate and dilute with 15 mL 1N HCl. Neutralize with saturated NaHCO$_3$ and extract with CH$_2$Cl$_2$. Wash the organic layer with saturated NaCl, dry with Na$_2$SO$_4$, concentrate, and purify (silica gel chromatography, eluting with EtOAc:CH$_2$CH$_2$ 50:50) to give the title compound as a tan solid (0.11 g; 53% yield). The free base product is converted to the methanesulfonate salt essentially as described in EXAMPLE 1.

MS (ES): m/z=420 [M+H].

The compounds of EXAMPLES 37-38 may be prepared essentially as described in EXAMPLE 36.

| EXAMPLE | Compound | MS (ES): m/z [M + H] |
|---|---|---|
| 37 | 5-(2-tert-Butyl-5-phenyl-3H-imidazol-4-yl)-3-(2,2-dimethyl-propyl)-2-methyl-3H-imidazo[4,5-b]pyridine methanesulfonate | 402 |
| 38 | 5-[2-(2-Chloro-6-fluorophenyl)-5-phenyl-3H-imidazol-4-yl]-3-(2,2-dimethyl-propyl)-2-methyl-3H-imidazo[4,5-b] pyridine methanesulfonate | 474 |

EXAMPLE 39

5-[2-(2,6-Difluorophenyl)-5-phenyl-3H-imidazol-4-yl]-3-(2,2-dimethylpropyl)-2-methyl-3H-imidazo[4,5-b]pyridine methanesulfonate Reduce {6-[2-(2,6-difluorophenyl)-5-phenyl-3H-imidazol-4-yl]-3-nitropyridin-2-yl}-(2,2-dimethylpropyl)amine essentially as described in EXAMPLE 16, and then react the diamine in trimethylorthoacatate as described in EXAMPLE 36 to give the free base as a tan solid (0.11 g; 49% yield). The methanesulfonate of the free base is formed essentially as described in EXAMPLE 1.

MS (ES): m/z=458 [M+H].

The compounds of EXAMPLES 40-45 may be prepared essentially as described in EXAMPLE 39.

| EXAMPLE | Compound | MS (ES): m/z [M + H] |
|---|---|---|
| 40 | 5-[2-(2,6-Difluorophenyl)-5-(4-fluorophenyl)-3H-imidazol-4-yl]-3-(2,2-dimethylpropyl)-2-methyl-3H-imidazo[4,5-b]pyridine methanesulfonate | 476 |
| 41 | 5-[2-(2,6-Dichlorophenyl)-5-(4-fluorophenyl)-3H-imidazol-4-yl]-3-(2,2-dimethylpropyl)-2-methyl-3H-imidazo[4,5-b]pyridine methanesulfonate | 508 |
| 42 | 3-Cyclopropylmethyl-5-[2-(2,6-difluorophenyl)-5-phenyl-3H-imidazol-4-yl]-2-methyl-3H-imidazo[4,5-b]pyridine methanesulfonate | 442 |
| 43 | 3-Cyclopropylmethyl-5-[2-(2,6-dichlorophenyl)-5-phenyl-3H-imidazol-4-yl]-2-methyl-3H-imidazo[4,5-b]pyridine methanesulfonate | 474 |

-continued

| EXAMPLE | Compound | MS (ES): m/z [M + H] |
|---|---|---|
| 44 | 5-(2-Cyclopropyl-5-phenyl-3H-imidazol-4-yl)-3-(2,2-dimethylpropyl)-2-methyl-3H-imidazo[4,5-b]pyridine methanesulfonate | 386 |
| 45 | 5-[2-(2,6-Dichlorophenyl)-5-phenyl-3H-imidazol-4-yl]-3-(2,2-dimethylpropyl)-2-methyl-3H-imidazo[4,5-b]pyridine methanesulfonate | 490 |

EXAMPLE 46

5-[2-(2-Chloro-6-fluorophenyl)-5-phenyl-3H-imidazol-4-yl]-3-(2,2-dimethylpropyl)-3H-imidazo[4,5-b]pyridine methanesulfonate Reduce {6-[2-(2-chloro-6-fluorophenyl)-5-phenyl-3H-imidazol-4-yl]-3-nitropyridin-2-yl}-(2,2-dimethylpropyl) amine essentially as described in EXAMPLE 15. React the diamine with refluxing neat triethylorthoformate for 24 h and at RT for an additional 24 h. Purify and isolate the free base essentially as described in EXAMPLE 36 (0.11 g, 49% yield). Convert to the methanesulfonate essentially as described in EXAMPLE 1.

MS (ES): m/z=460 [M+H].

The compounds of EXAMPLE 47-48 may be prepared essentially as described in EXAMPLE 46.

| EXAMPLE | Compound | MS (ES): m/z [M + H] |
|---|---|---|
| 47 | 5-(2-Cyclopropyl-5-phenyl-3H-imidazol-4-yl)-3-(2,2-dimethylpropyl)-3H-imidazo[4,5-b]pyridine methanesulfonate | 372 |
| 48 | 5-[2-(2,6-Difluorophenyl)-5-phenyl-3H-imidazol-4-yl]-3-isobutyl-3H-imidazo[4,5-b]pyridine methanesulfonate | 430 |

EXAMPLE 49

5-[3-(4-Fluorophenyl)-1-isopropylpyrazol-4-yl]-3H-3-isobutylimidazo[4,5-b]pyridin-2-ylamine di-methanesulfonate Add sodium hydrosulfite (2.55 g, 14.6 mmol) to a solution of 2-isobutylamino-3-nitro-6-[3-(4-fluorophenyl)-1-isopropylpyrazol-4-yl]pyridine (0.50 g, 1.27 mmol) in 25 mL of 1:1 THF:H$_2$O, in the presence of NH$_4$OH (8.70 mL, 32% in H$_2$O). Dilute with water (25 mL) after 2 h. Extract with EtOAc (100 mL), dry with MgSO$_4$, and concentrate. Dissolve the residue in 1:1 CH$_2$Cl$_2$:EtOH (25 mL), add cyanogen bromide (0.16 g, 1.51 mmol), and stir for about 48 h. Concentrate and purify the residue (silica gel chromatography, eluting with EtOAc:MeOH 16:1). Recrystallize from diethyl ether:hexanes to provide the free base (0.44 g, 88%). Convert to the methanesulfonate essentially as described in EXAMPLE 1 (58% yield).

MS (ES): m/z=393 [M+H].

The compounds of EXAMPLE 50-62 may be prepared essentially as described in EXAMPLE 49.

| EXAMPLE | Compound | MS (ES): m/z [M + H] |
|---|---|---|
| 50 | 5-[2-tert-Butyl-5-phenyl-1H-imidazol-4-yl]-3-isobutyl-3H-imidazo[4,5-b]pyridin-2-ylamine di-methanesulfonate | 389 |
| 51 | 5-[2-(2-Fluoro-6-chlorophenyl)-5-phenyl-1H-imidazol-4-yl]-3-isobutyl-3H-imidazo[4,5-b]pyridin-2-ylamine methanesulfonate | 461 |
| 52 | 5-[2-Cyclopropyl-5-phenyl-1H-imidazol-4-yl]-3-isobutyl-3H-imidazo[4,5-b]pyridin-2-ylamine methanesulfonate | 373 |
| 53 | 5-[2-(2-Fluoro-6-trifluoromethylphenyl)-5-phenyl-1H-imidazol-4-yl]-3-isobutyl-3H-imidazo[4,5-b]pyridin-2-ylamine methanesulfonate | 495 |
| 54 | 5-[2-(2-Fluoro-6-chlorophenyl)-5-(4-fluorophenyl-1H-imidazol-4-yl]-3-isobutyl-3H-imidazo[4,5-b]pyridin-2-ylamine methanesulfonate | 479 |
| 55 | 5-[2-isopropyl-5-phenyl-1H-imidazol-4-yl]-3-isobutyl-3H-imidazo[4,5-b]pyridin-2-ylamine di-methanesulfonate | 375 |
| 56 | 5-[2-(2-Fluoro-6-trifluoromethylphenyl)-5-(2,4-difluorophenyl-1H-imidazol-4-yl]-3-isobutyl-3H-imidazo[4,5-b]pyridin-2-ylamine methanesulfonate | 531 |
| 57 | 5-[2-tert-Butyl)-5-(2,4-difluorophenyl-1H-imidazol-4-yl]-3-isobutyl-3H-imidazo[4,5-b]pyridin-2-ylamine methanesulfonate | 425 |

-continued

| EXAMPLE | Compound | MS (ES): m/z [M + H] |
|---|---|---|
| 58 | 5-[2-Isopropyl)-5-(2,4-difluorophenyl-1H-imidazol-4-yl]-3-isobutyl-3H-imidazo[4,5-b]pyridin-2-ylamine methanesulfonate | 411 |
| 59 | 5-[2-(2-Fluoro-6-chlorophenyl)-5-(2,4-difluorophenyl-1H-imidazol-4-yl]-3-isobutyl-3H-imidazo[4,5-b]pyridin-2-ylamine methanesulfonate | 497 |
| 60 | 5-[2-Cyclopropyl-5-(2,4-difluorophenyl))-1H-imidazol-4-yl]-3-isobutyl-3H-imidazo[4,5-b]pyridin-2-ylamine methanesulfonate | 409 |
| 61 | 5-[2-Cyclopropyl-5-(4-fluorophenyl))-1H-imidazol-4-yl]-3-isobutyl-3H-imidazo[4,5-b]pyridin-2-ylamine di-methanesulfonate | 391 |
| 62 | 5-[2-tert-Butyl-5-(4-fluorophenyl)-1H-imidazol-4-yl]-3-isobutyl-3H-imidazo[4,5-b]pyridin-2-ylamine di-methanesulfonate | 407 |

EXAMPLE 63

N'-{5-[2-(2,6-Difluorophenyl)-5-phenyl-3H-imidazol-4-yl]-3-isobutyl-3H-imidazo[4,5-b]pyridin-2-yl}-N,N-dimethylformamidine Reflux N'-{5-[2-(2,6-difluorophenyl)-5-phenyl-3H-imidazol-4-yl]-3-isobutyl-3H-imidazo[4,5-b]pyridin-2-ylamine prepared essentially as described in EXAMPLE 1 (0.10 g, 0.225 mmol), N,N-dimethylformamide dimethyl acetal (0.05 mL, 0.4 mmol) in toluene (1.5 mL) for 2 h. Cool to RT and concentrate. Purify (silica gel chromatography, eluting with 1:1 $CH_2Cl_2$:acetonitrile) to give the title compound (0.11 g).

MS (ES): m/z=500 [M+H].

The compound of EXAMPLE 64 may be prepared essentially as described in EXAMPLE 63.

| EXAMPLE | Compound | MS (ES): m/z [M + H] |
|---|---|---|
| 64 | N'-{5-[2-(2,6-Dichlorophenyl)-5-phenyl-3H-imidazol-4-yl]-3-isobutyl-3H-imidazo[4,5-b]pyridin-2-yl}-N,N-dimethyl-formamidine | 533 |

EXAMPLE 65

N'-{5-[2-(2,6-Dichlorophenyl)-3-methyl-5-phenyl-3H-imidazol-4-yl]-3-isobutyl-3H-imidazo[4,5-b]pyridin-2-yl}-N,N-dimethylformamidine Stir N'-{5-[2-(2,6-dichlorophenyl)-5-phenyl-3H-imidazol-4-yl]-3-isobutyl-3H-imidazo[4,5-b]pyridin-2-yl}-N,N-dimethylformamidine prepared essentially as described in EXAMPLE 63 (0.10 g, 0.188 mmol), iodomethane (0.040 g, 0.282 mmol), and $Cs_2CO_3$ (0.09 g, 0.28 mmol) in DMF (1.5 mL) at RT for about 24 h. Extract with EtOAc and wash with water (3x), saturated aqueous NaCl, then dry over $Na_2SO_4$. Filter and concentrate to give a mixture of methyl isomers. Purify (silica gel chromatography) eluting with 1:1:0.4 $CH_2Cl_2$:acetonitrile:hexanes to give the title compound (0.02 g).

MS (ES): m/z=548 [M+H].

EXAMPLE 66

5-[2-(2,6-Difluorophenyl)-3-methyl-5-phenyl-3H-imidazol-4-yl]-3-isobutyl-3H-imidazo[4,5-b]pyridin-2-ylamine Heat N'-{5-[2-(2,6-difluorophenyl)-3-methyl-5-phenyl-3H-imidazol-4-yl]-3-isobutyl-3H-imidazo[4,5-b]pyridin-2-yl}-N,N-dimethylformamidine (0.02 g, 0.04 mol) in 1:1 glacial acetic acid:concentrated HCl (0.6 mL) at 100° C. for 30 min. Cool to RT. Add $CH_2Cl_2$ and water, neutralize with 5N NaOH to about pH=7 with rapid stirring. Extract the aqueous phase 3x with $CH_2Cl_2$, combine organic layers, wash with saturated aqueous NaCl and dry over $Na_2SO_4$. Filter and concentrate to give the title compound (0.02 g).

MS (ES): m/z=459 [M+H]

The compound of EXAMPLE 67 may be prepared essentially as described in EXAMPLE 66.

| EXAMPLE | Compound | MS (ES): m/z [M + H]) |
|---|---|---|
| 67 | 5-[2-(2,6-Dichlorophenyl)-3-methyl-5-phenyl-3H-imidazol-4-yl]-3-isobutyl-3H-imidazo[4,5-b]pyridin-2-ylamine | 493 |

EXAMPLE 68

3-(2,2-Dimethylpropyl)-5-(5-phenyl-3H-[1,2,3]triazol-4-yl)-3H-imidazo[4,5-b]pyridin-2-ylamine methanesulfonate Suspend (2,2-dimethyl-propyl)-[3-nitro-6-(5-phenyl-3H-[1,2,3]triazol-4-yl)pyridin-2-yl]amine (0.180 g, 0.51 mmol), and 10% Pd/C (0.025 g) in EtOH (10 μL) and stir at RT under a balloon containing hydrogen for 5 h. Filter the reaction mixture using a filtering agent and concentrate to approximately half the reaction volume. Use the diamine immediately without further isolation or purification (MS (ES): m/z 323 [M+H], and treat with cyanogen bromide (0.09 g) in EtOH (5 mL). Stir under nitrogen for 3.5 h, quench with saturated aqueous $NaHCO_3$ (2.0 mL), stir, dilute with $CH_2Cl_2$ (5 mL) and $H_2O$ (5 mL), and separate the phases. Extract the aqueous phase with $CH_2Cl_2$ (2x5 mL), wash the combined organic phases with 5 mL each of $H_2O$ and saturated aqueous NaCl, and dry with MgSO$_4$. Filter and concentrate. Purify the residue (silica gel chromatography, eluting with 4:96 2.0 N ammonia in MeOH:CH$_2$Cl$_2$) to give the free base. Convert to the methanesulfonate salt by treatment of a MeOH-water solution with methanesulfonic acid followed by lyophilization to give the title compound (0.07 g, 39%).

MS (ES): m/z=348 [M+H].

The compounds of EXAMPLE 69-71 may be prepared essentially as described in EXAMPLE 68.

| EXAMPLE | Compound | MS (ES): m/z [M + H]) |
|---|---|---|
| 69 | 3-(2,2-Dimethylpropyl)-5-[5-(4-fluoro-phenyl)-3H-[1,2,3]triazol-4-yl]-3H-imidazo[4,5-b]pyridin-2-ylamine methanesulfonate | 364 |
| 70 | 3-Cyclopropylmethyl-5-[5-(4-fluoro-phenyl)-3H-[1,2,3]triazol-4-yl]-3H-imidazo[4,5-b]pyridin-2-ylamine methanesulfonate | 350 |
| 71 | 3-Cyclopropylmethyl-5-(5-phenyl-3H-[1,2,3]triazol-4-yl)-3H-imidazo[4,5-b]pyridin-2-ylamine methanesulfonate | 332 |

EXAMPLE 72

5-[2-(2-Chloro-6-fluorophenyl)-5-phenyl-1H-imidazol-4-yl]-3-isobutyl-3H-[1,2,3]triazolo[4,5-b]pyridine methanesulfonate Add dropwise a solution of 6-[2-(2-chloro-6-fluorophenyl)-5-phenyl-1H-imidazol-4-yl]-N$^2$-isobutylpyridine-2,3-diamine (1.1 g, 2.52 mmol) in CH$_2$Cl$_2$ (9 mL) and 50% aqueous AcOH (9 mL) to a solution of sodium nitrite in water (0.1 mL) (0.184 g, 2.66 mmol). Stir the reaction mixture for 15 min, add additional CH$_2$Cl$_2$ and wash the organic layer with a saturated aqueous solution of NaCl, aqueous NaHCO$_3$ (5%), dry with MgSO$_4$, and concentrate. Purify the residue (silica gel chromatography, eluting with 4:1 to 1:2 hexane:EtOAc) to give the free base (70%). MS (ES): m/z=447 [M+H]. Add 0.34 mL of a 1 M solution of methanesulfonic acid in CH$_2$Cl$_2$:MeOH 9:1 to a solution of the free base (0.15 g, 0.336 mmol) in 10 mL CH$_2$Cl$_2$:MeOH 9:1. Stir the solution 5 min, concentrate, and triturate the white solid in diethyl ether. Filter the solid to provide the title compound (71%).

MS (ES): m/z=447 [M+H].

The compounds of EXAMPLE 73-75 may be prepared essentially as described in EXAMPLE 72.

| EXAMPLE | Compound | MS (ES): m/z [M + H]) |
|---|---|---|
| 73 | 5-[2-(2,6-Dichlorophenyl)-5-phenyl-1H-imidazol-4-yl]-3-isobutyl-3H-[1,2,3]triazolo[4,5-b]pyridine methanesulfonate | 463 |
| 74 | 5-[2-(2,6-Dichlorophenyl)-5-(2,4-difluoro-phenyl)-1H-imidazol-4-yl]-3-isobutyl-3H-[1,2,3]triazolo[4,5-b]pyridine methanesulfonate | 499 |
| 75 | 5-[2-tert-Butyl-5-(4-fluorophenyl)-1H-imidazol-4-yl]-3-isobutyl-3H-[1,2,3]triazolo[4,5-b]pyridine methanesulfonate | 393 |

EXAMPLE 76

2-Amino-5-(2-tert-butyl-5-phenyl-3H-imidazol-4-yl)imidazo[4,5-b]pyridine-3-sulfonic acid dimethylamide methanesulfonate Heat a mixture of 2-amino-5-(2-oxo-2-phenylacetyl)imidazo[4,5-b]pyridine-3-sulfonic acid dimethylamide (0.07 g, 0.20 mmol), trimethylacetaldehyde (65 μl, 0.6 mmol) and ammonium acetate (0.23 g, 3 mmol) in AcOH (5 mL) at 90° C. for 4 h. Cool to RT. Dilute with a saturated aqueous NaHCO$_3$, and extract with EtOAc. Concentrate the organic phase and purify (silica gel chromatography, eluting with 15:1 CH$_2$Cl$_2$:MeOH) to give the free base (35%). MS (ES): m/z=438 [M+H]. Add 5.4 μl of a solution 1 M methanesulfonic acid in CH$_2$Cl$_2$:MeOH 95:5 to a solution of the free base (0.02 g, 0.054 mmol) in 5 mL CH$_2$Cl$_2$:MeOH 95:5. Stir the solution 5 min, concentrate, and triturate the white solid in diethyl ether. Filter the solid to give the title compound (71%).

MS (ES): m/z=440 [M+H].

The compounds of EXAMPLE 77-79 may be prepared essentially as described in EXAMPLE 76.

| EXAMPLE | Compound | MS (ES): m/z [M + H]) |
|---|---|---|
| 77 | 2-Amino-5-[(2-fluoro-6-chlorophenyl)-5-phenyl-3H-imidazol-4-yl)]imidazo[4,5-b]pyridine-3-sulfonic acid dimethylamide methanesulfonate | 512 |
| 78 | 2-Amino-5-[(2,6-dichlorophenyl)-5-phenyl-3H-imidazol-4-yl)]imidazo[4,5-b]pyridine-3-sulfonic acid dimethylamide methanesulfonate | 528 |
| 79 | 2-Amino-5-(2-tert-butyl-5-(2,4-difluoro-phenyl)-3H-imidazol-4-yl)imidazo[4,5-b]pyridine-3-sulfonic acid dimethylamide methanesulfonate | 476 |

EXAMPLE 80

5-[2-(2,6-Difluorophenyl)-5-phenyl-3H-imidazol-4-yl]-3-(propane-2-sulfonyl)-3H-imidazo[4,5-b]pyridin-2-ylamine methanesulfonate Stir a mixture of propane-2-sulfonic acid {3-amino-6-[2-(2,6-difluorophenyl)-5-phenyl-3H-imidazol-4-yl]-pyridin-2-yl}amide (0.37 g, 0.79 mmol), cyanogen bromide (0.104 g, 0.99 mmol) and lithium methoxide (0.033 g, 0.87 mmol) in methylene chloride (10 mL) for 12 h at RT. Add saturated NaHCO$_3$ (10 mL) and stir for 1 h. Separate the layers and extract with saturated aqueous NaCl. Dry the organic layer over NaSO$_4$, concentrate and purify (silica gel chromatography, eluting with a gradient of 40:60 EtOAC:hexanes to 80:20 EtOAc:hexanes) to give the free base (0.21 g, 54%). MS (ES): m/z=495 [M+H]. Add methanesulfonic acid to a solution of the free base in 1 mL of a 5:1 mixture of methanol:methylene chloride. Concentrate the solution and add diethyl ether. Filter the solid, and dry to give the title compound.

MS (ES): m/z=495 [M+H].

The compounds of EXAMPLE 81-91 may be prepared essentially as described in EXAMPLE 80.

| EXAMPLE | Compound | MS (ES): m/z (M + H) |
|---|---|---|
| 81 | 3-Butyl-5-[2-(2,6-difluorophenyl)-5-phenyl-3H-imidazol-4-yl]-3H-imidazo[4,5-b]pyridin-2-ylamine methanesulfonate | 445 |
| 82 | 3-Butyl-5-[2-(2-fluorophenyl)-5-phenyl-3H-imidazol-4-yl]-3H-imidazo[4,5-b]pyridin-2-ylamine, di-methanesulfonate | 427 |
| 83 | 3-Butyl-5-[2-(2-chloro-6-fluorophenyl)-5-phenyl-3H-imidazol-4-yl]-3H-imidazo[4,5-b]pyridin-2-ylamine methanesulfonate | 461 |
| 84 | 3-Butyl-5-(2-tert-butyl-5-phenyl-3H-imidazol-4-yl)-3H-imidazo[4,5-b]pyridin-2-ylamine methanesulfonate | 389 |
| 85 | 3-Butyl-5-[2-(2-fluoro-6-trifluoromethylphenyl)-5-phenyl-3H-imidazol-4-yl]-3H-imidazo[4,5-b]pyridin-2-ylamine methanesulfonate | 495 |
| 86 | 2-Amino-5-(5-(phenyl-2H-[1,2,3]triazol-4-yl)imidazo[4,5-b]pyridine-3-sulfonic acid dimethylamide | 385 |
| 87 | 5-[2-(2-Fluoro-6-trifluoromethylphenyl)-5-phenyl-3H-imidazol-4-yl]-3-(propane-2-sulfonyl)-3H-imidazo[4,5-b]pyridin-2-ylamine methanesulfonate | 545 |
| 88 | 5-(2-tert-Butyl-5-phenyl-3H-imidazol-4-yl)-3-(propane-2-sulfonyl)-3H-imidazo[4,5-b]pyridin-2-ylamine methanesulfonate | 439 |
| 89 | 5-[2-(2,6-Dichlorophenyl)-5-phenyl-3H-imidazol-4-yl]-3-(propane-2-sulfonyl)-3H-imidazo[4,5-b]pyridin-2-ylamine methanesulfonate | 529 |
| 90 | 5-[2-(2-Chloro-6-fluorophenyl)-5-phenyl-3H-imidazol-4-yl]-3-(propane-2-sulfonyl)-3H-imidazo[4,5-b]pyridin-2-ylamine methanesulfonate | 511 |
| 91 | 3-Butyl-5-[2-tert-butyl-5-(2,4-difluorophenyl)-3H-imidazol-4-yl]-3H-imidazo[4,5-b]pyridin-2-ylamine methanesulfonate | 425 |

EXAMPLE 92

5-[2-tert-Butyl-4-(4-fluorophenyl)oxazol-5-yl]-3-isobutyl-3H-imidazo[4,5-b]pyridin-2-ylamine Bubble with nitrogen a suspension of 2-tert-butyl-4-(4-fluorophenyl)oxazole (0.145 g, 0.66 mmol), 5-bromo-3-isobutyl-3H-imidazo[4,5-b]pyridin-2-ylamine (0.355 g, 1.32 mmol), cesium carbonate (6.06 g, 18.6 mmol), palladium (II) acetate (0.201 g, 10%) and triphenylphosphine (0.14 g, 0.07 mmol) in DMF (1.5 mL). Heat the reaction at 100° C. overnight, cool to RT and partition between EtOAc and saturated aqueous NaCl. Wash the organic layer with saturated aqueous NaCl. Dry with $Na_2SO_4$, filter, concentrate, and purify (silica gel chromatography, eluting with 2% of 2M ammonia/MeOH in $CH_2Cl_2$ to give the title compound (0.07 g, 34%).

MS (ES): m/z=408 [M+H].

The compounds of EXAMPLE 93-96 may be prepared essentially as described in EXAMPLE 92, with the free base converted to the methansulfonate essentially as described in EXAMPLE 1.

| EXAMPLE | Compound | MS (ES): m/z (M + H) |
|---|---|---|
| 93 | 5-[2-tert-Butyl-4-(2,4-difluorophenyl)oxazol-5-yl]-3-isobutyl-3H-imidazo[4,5-b]pyridin-2-ylamine methanesulfonate | 426 |
| 94 | 5-[4-(4-Fluorophenyl)-2-isopropyloxazol-5-yl]-3-isobutyl-3H-imidazo[4,5-b]pyridin-2-ylamine methanesulfonate | 394 |
| 95 | 3-Isobutyl-5-(2-methyl-4-phenylthiazol-5-yl)-3H-imidazo[4,5-b]pyridin-2-ylamine methanesulfonate | 364 |

-continued

| EXAMPLE | Compound | MS (ES): m/z (M + H) |
|---|---|---|
| 96 | 5-[4-(4-Fluorophenyl)-2-methylthiazol-5-yl]-3-isobutyl-3H-imidazo[4,5-b]pyridin-2-ylamine methanesulfonate | 382 |

EXAMPLE 97

2-Amino-5-(2-tert-butyl-5-(4-fluorophenyl)oxazol-5-yl)imidazo[4,5-b]pyridine-3-sulfonic acid dimethylamide Dissolve 2-amino-5-bromoimidazo[4,5-b]pyridine-3-sulfonic acid dimethylamide (0.05 g, 0.156 mmol) in toluene (3 ml) in a sealed tube. Add 2-tert-butyl-4-(4-fluorophenyl)-5-trimethylstannanyloxazole (0.07 g, 0.17 mmol) and tetrakis (triphenylphosphine)palladium (0) (0.02 g, 0.015 mmol). Heat the mixture at 110° C. for 4 h. Concentrate and purify (silica gel chromatography, eluting with 20:1 $CH_2Cl_2$:MeOH) to give the title compound. (14%).

MS (ES): m/z=459 [M+H].

The compound in EXAMPLE 98 may be prepared essentially as described in EXAMPLE 97, with the free base converted to the methanesulfonate essentially as described in EXAMPLE 1.

| EXAMPLE | Compound | MS (ES): m/z (M + H) |
|---|---|---|
| 98 | 2-Amino-5-(2-ispropyl-5-(4-fluorophenyl)oxazol-5-yl)imidazo[4,5-b]pyridine-3-sulfonic acid dimethylamide methanesulfonate | 445 |

EXAMPLE 99

5-[2-(2,6-Dichloro-phenyl)-5-(4-fluoro-phenyl)-1H-imidazol-4-yl]-3-(2,2-dimethyl-propyl)-3H-imidazo[4,5-b]pyridin-2-ylamine methanesulfonate Mix 1-[2-amino-3-(2,2-dimethyl-propyl)-3H-imidazo[4,5-b]pyridin-5-yl]-2-(4-fluoro-phenyl)-ethane-1,2-dione (19.58 g, 55.24 mmol), 2,6-dichloro-benzaldehyde (15.47 g; 88.39 mmol) and NH$_4$OAc (42.58 g, 552.41 mmol) in glacial acetic acid (200 mL) and stir at 85° C. under nitrogen for 5 h. Concentrate the resulting reaction mixture under reduced pressure. Dissolve the residue in ethyl acetate (2,000 mL) and wash the resulting solution with saturated aqueous sodium bicarbonate (2×1,000 mL each), water (1,000 mL), and saturated aqueous sodium chloride (1,000 mL). Dry the organics over MgSO$_4$, filter, and then concentrate under reduced pressure. Purify by column chromatography, eluting with ethyl acetate-hexanes (1:1), then ethyl acetate hexanes (2:1), then neat ethyl acetate, then 5% of 2N NH$_3$/MeOH in ethyl acetate to give 11.70 g (41.5% yield) of 5-[2-(2,6-dichloro-phenyl)-5-(4-fluoro-phenyl)-1H-imidazol-4-yl]-3-(2,2-dimethyl-propyl)-3H-imidazo[4,5-b]pyridin-2-ylamine as an off-white solid. MS (ES+): m/z=509 (M+1).

Mix 5-[2-(2,6-dichloro-phenyl)-5-(4-fluoro-phenyl)-1H-imidazol-4-yl]-3-(2,2-dimethyl-propyl)-3H-imidazo[4,5-b]pyridin-2-ylamine (11.20 g, 21.99 mmol) in methanol (150 mL), and then add a solution of methanesulfonic acid (2.11 g, 21.96 mmol) in methanol (10 mL) dropwise. Stir at room temperature for 20 minutes and then concentrate under reduced pressure. Add ethyl acetate (150 mL), filter resulting slurry, and wash filter cake with diethyl ether (200 mL). Dry the resulting solid in a drying oven at 80° C. under house vacuum for 2 h to give 12.765 g (95% yield) of the title compound as a light-purple solid.

$^1$H-NMR (400 MHz; CD$_3$OD): δ 7.78-7.50 (m, 7H), 7.24-7.20 (m, 2H), 3.86 (s, 2H), 2.70 (s, 3H), 0.85 (s, 9H)

TOF-MS [ES+, M+H] Obs. m/z 509.1412, Calc. m/z 509.1423.

EXAMPLE 100

3-(2,2-Dimethyl-propyl)-5-[5-(4-fluoro-phenyl)-2-(2-fluoro-6-trifluoromethyl-phenyl)-1H-imidazol-4-yl]-3H-imidazo[4,5-b]pyridin-2-ylamine methanesulfonate Mix 1-[2-amino-3-(2,2-dimethyl-propyl)-3H-imidazo[4,5-b]pyridin-5-yl]-2-(4-fluoro-phenyl)-ethane-1,2-dione (18.32 g, 51.69 mmol) and 2-fluoro-6-trifluoromethyl-benzaldehyde (15.00 g, 78.08 mmol) and NH$_4$OAc (39.84 g, 516.90 mmol) in glacial acetic acid (200 mL) and stir at 85° C. under nitrogen for 4 h. Concentrate the resulting reaction mixture under reduced pressure. Dissolve the residue in ethyl acetate (2,000 mL) and wash the resulting solution with saturated aqueous NaHCO$_3$ (2×1,000 mL each), water (1,000 mL), and saturated aqueous sodium chloride (1,000 mL). Dry the organics over MgSO$_4$, filter, and then concentrate under reduced pressure. Purify by column chromatography, eluting with neat ethyl acetate, then 2% of 2N ammonia/MeOH in ethyl acetate, then 5% of 2N ammonia/MeOH in ethyl acetate to give 7.38 g 3-(2,2-dimethyl-propyl)-5-[5-(4-fluoro-phenyl)-2-(2-fluoro-6-trifluoromethyl-phenyl)-1H-imidazol-4-yl]-3H-imidazo[4,5-b]pyridin-2-ylamine as an off-white solid. Purify the impure fractions by column chromatography, eluting with neat ethyl acetate, then 1% of 2N ammonia/MeOH in ethyl acetate, then 2% of 2N ammonia/MeOH in ethyl acetate, then 3% of 2N ammonia/MeOH in ethyl acetate) to give an additional 4.68 g of the desired compound.

MS(ES+): m/z=527 (M+1)

Mix 3-(2,2-dimethyl-propyl)-5-[5-(4-fluoro-phenyl)-2-(2-fluoro-6-trifluoromethyl-phenyl)-1H-imidazol-4-yl]-3H-imidazo[4,5-b]pyridin-2-ylamine (11.56 g, 21.95 mmol) in methanol (150 mL), and then add a solution of methanesulfonic acid (2.11 g, 21.96 mmol) in MeOH (10 mL) dropwise. Allow the resulting reaction mixture to stir at room temperature for 20 minutes, then concentrate under reduced pressure. Slurry the residue in diethyl ether, filter, and wash with fresh diethyl ether. Dry the resulting solid in a drying oven at room temperature under house vacuum for 48 h to give 12.015 g (87.9% yield) of the title compound as a light-purple solid.

$^1$H-NMR (400 MHz; CD$_3$OD): δ 7.84-7.60 (m, 7H), 7.24-7.20 (m, 2H), 3.86 (s, 2H), 2.70 (s, 3H), 0.85 (s, 9H)

TOF-MS [ES+, M+H] Obs. m/z 527.1979, Calc. m/z 527.1982.

EXAMPLE 101

5-[2-tert-Butyl-5-(2,4-difluoro-phenyl)-1H-imidazol-4-yl]-3-(2,2-dimethyl-propyl)-3H-imidazo[4,5-b]pyridin-2-ylamine methanesulfonate Mix 1-[2-amino-3-(2,2-dimethyl-propyl)-3H-imidazo[4,5-b]pyridin-5-yl]-2-(2,4-difluoro-phenyl)-ethane-1,2-dione (17.36 g, 46.62 mmol) and trimethylacetaldehyde (6.42 g, 74.53 mmol) and NH$_4$OAc (35.93 g, 466.20 mmol) in glacial acetic acid (200 mL) and stir at 85° C. under nitrogen for 4.5 h. Cool to room temperature overnight. Heat the reaction at 85° C. for 5 h, then 100° C. for 3 h, then cool to room temperature overnight. Concentrate the resulting reaction mixture under reduced pressure. Dissolve the residue in EtOAc (2 L) and wash the resulting solution with saturated NaHCO$_3$ (2×1 L), H$_2$O (1 L), and saturated aqueous sodium chloride (1 L). Dry the organics over Na$_2$SO$_4$, filter, and then concentrate under reduced pressure. Purify by column chromatography, eluting with neat EtOAc, then 1% of 2N ammonia/MeOH in EtOAc, then 2% of 2N ammonia/MeOH in EtOAc, then 3% of 2N ammonia/MeOH in EtOAc) to give 10.28 g of 5-[2-tert-butyl-5-(2,4-difluoro-phenyl)-1H-imidazol-4-yl]-3-(2,2-dimethyl-propyl)-3H-imidazo[4,5-b]pyridin-2-ylamine as an off-white solid.

MS (ES+): m/z=439 (M+1)

Mix 5-[2-tert-butyl-5-(2,4-difluoro-phenyl)-1H-imidazol-4-yl]-3-(2,2-dimethyl-propyl)-3H-imidazo[4,5-b]pyridin-2-ylamine (11.55 g, 26.33 mmol) in MeOH (150 mL), and then add a solution of methanesulfonic acid (2.53 g, 26.33 mmol) in MeOH (10 mL) dropwise. Stir the resulting reaction mixture at room temperature for 20 minutes, then concentrate under reduced pressure. Slurry the residue in Et$_2$O, then filter and wash with fresh Et$_2$O. Dry the resulting solid in a drying oven at room temperature under house vacuum overnight, then at 80° C. for 1.5 h. Dissolve the salt in MeOH and then treat with NaHCO$_3$ until basic. Extract the resulting solution with EtOAc, dry the combined organics over Na$_2$SO$_4$, filter, then concentrate under reduced pressure. Purify by column chromatography, eluting with neat EtOAc, then 1% of 2N ammonia/MeOH in EtOAc, then 2% of 2N ammonia/MeOH in EtOAc to give 9.38 g of 5-[2-tert-butyl-5-(2,4-difluoro-phenyl)-1H-imidazol-4-yl]-3-(2,2-dimethyl-propyl)-3H-imidazo[4,5-b]pyridin-2-ylamine. Mix 5-[2-tert-butyl-5-(2, 4-difluoro-phenyl)-1H-imidazol-4-yl]-3-(2,2-dimethyl-propyl)-3H-imidazo[4,5-b]pyridin-2-ylamine (9.38 g, 21.39 mmol) in anhydrous MeOH (150 mL), and then add a solution of methanesulfonic acid (2.06 g, 21.43 mmol) in MeOH (10 mL) dropwise. Allow the resulting reaction mixture to stir at room temperature for 30 minutes, then concentrate under reduced pressure. Slurry the residue in $Et_2O$, then filter and wash with fresh $Et_2O$. Dry the resulting solid in a drying oven at room temperature under house vacuum for 48 h to give 10.695 g (76% yield) of the title compound as a tan solid.

$^1$H-NMR (400 MHz; $CD_3OD$): δ 7.74-7.66 (m, 2H), 7.60-7.54 (m, 1H), 7.15-7.08 (m, 2H), 3.70 (s, 2H), 2.70 (s, 3H), 1.51 (s, 9H), 0.81 (s, 9H)

TOF-MS [ES+, M+H]: Obs.: m/z=439.2398; Calc.: m/z=439.2422

EXAMPLE 102

5-[2-tert-Butyl-5-(4-fluoro-phenyl)-1H-imidazol-4-yl]-3-(2,2-dimethyl-propyl)-3H-imidazo[4,5-b]pyridin-2-ylamine methanesulfonate Stir a suspension of {6-[2-tert-Butyl-5-(4-fluoro-phenyl)-3H-imidazol-4-yl]-3-nitro-pyridin-2-yl}-(2,2-dimethylpro-pyl)-amine (426 mg, 1.0 mmol) and 10% palladium on carbon (85 mg) in 100% ethanol under hydrogen from a balloon overnight. Filter the suspension through a 0.2 μm syringe filter and concentrate under reduced pressure. Dissolve the residue in 10% aqueous ethanol and treat at room temperature with cyanogen bromide (80 mg, 0.75 mmol, 1.5 equiv). When the reaction is complete, quench the reaction with saturated aqueous $NaHCO_3$. Add ethyl acetate and water to dissolve all solids. Wash the organic layer once with saturated aqueous $NaHCO_3$, once with saturated aqueous NaCl, dry with $Na_2SO_4$, filter, and concentrate under reduced pressure. Subject the residue to medium pressure silica gel chromatography eluting with 50% ethyl acetate/$CH_2Cl_2$ then with a gradient of 1.5-3.5% (2M ammonia in MeOH)/$CH_2Cl_2$) to provide 5-[2-tert-butyl-5-(4-fluoro-phenyl)-1H-imidazol-4-yl]-3-(2,2-dimethyl-propyl)-3H-imidazo[4,5-b]pyridin-2-ylamine as a brown foam (156 mg, 74% yield).

Treat a solution of 5-[2-tert-butyl-5-(4-fluoro-phenyl)-1H-imidazol-4-yl]-3-(2,2-dimethyl-propyl)-3H-imidazo[4,5-b]pyridin-2-ylamine in methanol-water with methanesulfonic acid followed by lyophilization to provide the title compound.

Exact MS calc.: m/z=421.2516 (M+H)$^+$; found: m/z=421.2523 (M+H)$^+$.

$^1$H-NMR (DMSO-$d_6$): δ 7.85 (d, 1H, J=7.9 Hz), 7.85 (d, 1H, J=7.9 Hz), 7.72 (d, 1H, J=8.4 Hz), 7.62 (dd, 2H, J=8.8, 4.8 Hz), 7.27 (t, 2H, J=8.8 Hz), 3.90 (s, 2H), 2.70 (s, 3H), 1.62 (s, 9H), 0.89 (s, 9H)

EXAMPLE 103

5-[2-tert-Butyl-5-(4-fluoro-phenyl)-1H-imidazol-4-yl]-3-(2,2-dimethyl-propyl)-3H-imidazo[4,5-b]pyridin-2-ylamine fumarate Dissolve 126 mg (0.3 mmol) 5-[2-tert-butyl-5-(4-fluoro-phenyl)-1H-imidazol-4-yl]-3-(2,2-dimethyl-propyl)-3H-imidazo[4,5-b]pyridin-2-ylamine in 1.0 ml 88% acetone*. Add a solution of 70 mg fumaric acid in warm 88% acetone* incrementally with shaking. Add seed crystals and filter the resultant precipitate. Air dry to provide 145 mg (74%) of slight purple hair-like crystals.

*(remainder water by volume)

EXAMPLE 104

Crystalline 5-[2-tert-Butyl-5-(4-fluoro-phenyl)-1H-imidazol-4-yl]-3-(2,2-dimethyl-propyl)-3H-imidazo [4,5-b]pyridin-2-ylamine dimethanesulfonate Dissolve 126 mg (0.3 mmol) 5-[2-tert-butyl-5-(4-fluoro-phenyl)-1H-imidazol-4-yl]-3-(2,2-dimethyl-propyl)-3H-imidazo[4,5-b]pyridin-2-ylamine in 2.0 ml acetone. Add 58 mg methanesulfonic acid incrementally. Add seed crystals and filter the resultant precipitate. Air dry to provide 114 mg (62%) of off-white irregular crystals.

m.p.>250° C.

EXAMPLE 105

Amorphous 5-[2-tert-Butyl-5-(4-fluoro-phenyl)-1H-imidazol-4-yl]-3-(2,2-dimethyl-propyl)-3H-imidazo [4,5-b]pyridin-2-ylamine dimethanesulfonate Dissolve 5-[2-tert-butyl-5-(4-fluoro-phenyl)-1H-imidazol-4-yl]-3-(2,2-dimethyl-propyl)-3H-imidazo[4,5-b]pyridin-2-ylamine dimethanesulfonate (300 mg) in 5 mL deionized water. Filter solution through a 0.45 μm filter into a pre-chilled 500 mL volumetric flask. Rapidly freeze solution on bottom and sides of flask. Freeze dry for 24 hours to provide amorphous 5-[2-tert-butyl-5-(4-fluoro-phenyl)-1H-imidazol-4-yl]-3-(2,2-dimethyl-propyl)-3H-imidazo[4,5-b] pyridin-2-ylamine dimethanesulfonate.

EXAMPLE 106

5-[2-tert-Butyl-5-(4-fluoro-phenyl)-1H-imidazol-4-yl]-3-(2,2-dimethyl-propyl)-3H-imidazo[4,5-b]pyridin-2-ylamine succinate Dissolve 126 mg (0.3 mmol) 5-[2-tert-butyl-5-(4-fluoro-phenyl)-1H-imidazol-4-yl]-3-(2,2-dimethyl-propyl)-3H-imidazo[4,5-b]pyridin-2-ylamine in 2.0 mL 88% acetone*. Add a solution of 71 mg succinic acid in 1 mL warm 88% acetone* incrementally. Add seed crystals and filter the resultant precipitate. Air dry to provide 123 mg (63%) of very light purple crystals.

*(remainder water by volume)

EXAMPLE 107

5-[2-tert-Butyl-5-(4-fluoro-phenyl)-1H-imidazol-4-yl]-3-(2,2-dimethyl-propyl)-3H-imidazo[4,5-b]pyridin-2-ylamine dimaleate Dissolve 126 mg (0.3 mmol) 5-[2-tert-butyl-5-(4-fluoro-phenyl)-1H-imidazol-4-yl]-3-(2,2-dimethyl-propyl)-3H-imidazo[4,5-b]pyridin-2-ylamine in 1.0 mL isopropanol. Add a solution of 69.6 mg maleic acid in 1 mL warm isopropanol incrementally. Add seed crystals and filter the resultant precipitate. Air dry to provide 120 mg (63%) of very light purple crystals.

EXAMPLE 108

5-[2-tert-Butyl-5-(4-fluoro-phenyl)-1H-imidazol-4-yl]-3-(2,2-dimethyl-propyl)-3H-imidazo[4,5-b]pyridin-2-ylamine dihydrochloride Dissolve 126 mg (0.3 mmol) 5-[2-tert-butyl-5-(4-fluoro-phenyl)-1H-imidazol-4-yl]-3-(2,2-dimethyl-propyl)-3H-imidazo[4,5-b]pyridin-2-ylamine in 2.0 mL acetone. Add 120 μL of 5N hydrochloric acid incrementally. Filter the resultant precipitate. Air dry to provide 140 mg (93%) of very light pink crystals.

EXAMPLE 109

5-[2-(2-Chloro-6-fluoro-phenyl)-5-phenyl-3H-imidazol-4-yl]-3-(2,2-dimethylpropyl)-3H-imidazo[4,5-b]pyridin-2-ylamine methanesulfonate Dissolve {6-[2-(2-chloro-6-fluoro-phenyl)-5-phenyl-3H-imidazol-4-yl]-3-nitro-pyridin-2-yl}-(2,2-dimethylpropyl)-amine (240 mg, 0.50 mmol) in 100% ethanol (10 mL) and add tin(II) dichloride dihydrate (564 mg, 2.50 mmol, 5.0 equiv). Heat the reaction mixture until starting material is consumed. Cool the reaction solution to room temperature, quench slowly with saturated aqueous $NaHCO_3$. Add Celite® to the quenched reaction and filter the suspension on a Celite® pad with water and ethyl acetate washes. Separate the layers and wash the organic layer with saturated aqueous NaCl. Dry the organic layer with $Na_2SO_4$, filter, and concentrate under reduced pressure. Add 10% aqueous ethanol and cyanogen bromide (106 mg, 1.00 mmol, 2.0 equiv) to the resulting solid and stir overnight. Quench the reaction with saturated aqueous $NaHCO_3$ (20 mL). Add ethyl acetate and water to dissolve all solids. Wash the organic layer three times with saturated aqueous NaCl, dry with $Na_2SO_4$, filter, and concentrate under reduced pressure. Subject the residue to medium pressure silica gel chromatography eluting with a gradient of 1.5-3% (2M ammonia in MeOH)/$CH_2Cl_2$ to provide 5-[2-(2-Chloro-6-fluoro-phenyl)-5-phenyl-3H-imidazol-4-yl]-3-(2,2-dimethylpropyl)-3H-imidazo[4,5-b]pyridin-2-ylamine as a yellow-green solid (196 mg, 60% yield).

Treat a solution of 5-[2-(2-Chloro-6-fluoro-phenyl)-5-phenyl-3H-imidazol-4-yl]-3-(2,2-dimethylpropyl)-3H-imidazo[4,5-b]pyridin-2-ylamine in methanol-water with methanesulfonic acid followed by lyophilization to provide the title compound.

MS (ESI): m/z=475.2 $(M+H)^+$.

EXAMPLE 110

5-[2-tert-Butyl-5-(4-fluoro-phenyl)-3H-imidazol-4-yl]-3-(1(R),2,2-trimethyl-propyl)-3H-imidazo[4,5-b]pyridin-2-ylamine methanesulfonate Dissolve {6-[2-tert-butyl-5-(4-fluoro-phenyl)-3H-imidazol-4-yl]-3-nitro-pyridin-2-yl}-(1(R),2,2-trimethyl-propyl)-amine (558 mg, 1.27 mmol) in 100% ethanol (15 mL) and add tin(II) dichloride dihydrate (1.4 g, 6.3 mmol, 5 equiv). Heat the reaction mixture until starting material is consumed. Cool the reaction solution to room temperature, quench slowly with saturated aqueous $NaHCO_3$. Add Celite® and filter the suspension on a Celite® pad, washing with water and ethyl acetate. Separate the layers and wash the organic layer with saturated aqueous NaCl. Dry the organic layer with $Na_2SO_4$, filter, and concentrate under reduced pressure. Add 10% aqueous ethanol (13 mL) and cyanogen bromide (202 mg, 1.99 mmol, 1.5 equiv) to the residue and stir overnight. Add another 1.5 equiv of cyanogen bromide, stir 3 h, and quench with saturated aqueous $NaHCO_3$ (20 mL). Add ethyl acetate and water to dissolve all solids. Wash the organic layer three times with saturated aqueous NaCl, dry with $Na_2SO_4$, filter, and concentrate under reduced pressure. Subject the residue to medium pressure silica gel chromatography eluting with a gradient of 1.5-4% (2M ammonia in MeOH)/$CH_2Cl_2$ to provide 5-[2-tert-Butyl-5-(4-fluoro-phenyl)-3H-imidazol-4-yl]-3-((R),2,2-trimethyl-propyl)-3H-imidazo[4,5-b]pyridin-2-ylamine as a tan glass (158 mg, 29% yield).

Treat a solution of 5-[2-tert-butyl-5-(4-fluoro-phenyl)-3H-imidazol-4-yl]-3-(1(R),2,2-trimethyl-propyl)-3H-imidazo[4,5-b]pyridin-2-ylamine in methanol-water with methanesulfonic acid followed by lyophilization to provide the title compound.

MS (ESI): m/z=435.2 (M+H)+

EXAMPLE 111

5-[2-(2,6-Difluoro-phenyl)-5-(4-fluoro-phenyl)-3H-imidazol-4-yl]-3-(1(R), 2,2-trimethyl-propyl)-3H-imidazo[4,5-b]pyridin-2-ylamine methanesulfonate Dissolve {6-[2-(2,6-difluoro-phenyl)-5-(4-fluoro-phenyl)-3H-imidazol-4-yl]-3-nitro-pyridin-2-yl}-(1(R),2,2-trimethyl-propyl)-amine (673 mg, 1.4 mmol) in 100% ethanol (15 mL) and add tin(II) dichloride dihydrate (1.5 g, 6.8 mmol, 5 equiv). Heat the reaction mixture until starting material is consumed. Cool the reaction solution to room temperature, quench slowly with saturated aqueous $NaHCO_3$. Add Celite® to the quenched reaction and filter the suspension on a Celite® pad, washing with water and ethyl acetate. Separate the layers and wash the organic layer with saturated aqueous NaCl. Dry the organic layer with $Na_2SO_4$, filter, and concentrated under reduced pressure. Add 10% aqueous ethanol (14 mL) and cyanogen bromide (216 mg, 2.04 mmol, 1.5 equiv) to the residue and stir overnight. Quench with saturated aqueous $NaHCO_3$ (20 mL). Add ethyl acetate and water to dissolve all solids. Wash the organic layer is with saturated aqueous NaCl, dry with $Na_2SO_4$, filter, and concentrate under reduced pressure. Subject the residue to medium pressure silica gel chromatography eluting with a gradient of 1.5-3% (2M ammonia in MeOH)/$CH_2Cl_2$ to provide 5-[2-(2,6-difluoro-phenyl)-5-(4-fluoro-phenyl)-3H-imidazol-4-yl]-3-(1(R),2,2-trimethyl-propyl)-3H-imidazo[4,5-b]pyridin-2-ylamine as a tan glass (289 mg, 43% yield).

Treat a solution of 5-[2-(2,6-difluoro-phenyl)-5-(4-fluoro-phenyl)-3H-imidazol-4-yl]-3-(1(R),2,2-trimethyl-propyl)-3H-imidazo[4,5-b]pyridin-2-ylamine in methanol-water with methanesulfonic acid followed by lyophilization to provide the title compound.

MS (ESI): m/z=491.2 $(M+H)^+$

EXAMPLE 112

5-[2-tert-butyl-5-(4-fluoro-phenyl)-1H-imidazol-4-yl]-3-(2,2-dimethyl-propyl)-3H-imidazo[4,5-b]pyridin-2-ylamine dimethanesulfonate 5-Bromo-3-(2,2-dimethyl-propyl)-3H-imidazo[4,5-b]pyridin-2-yl-ammonium bromide Stir a mixture of hypophosphorous acid 50 wt. % aq. sol'n (0.555 g) and 5% Pt/C (2.5 g) in $H_2O$ (20 mL, 0.4 vol.) for 10 minutes. Add solid $VO(acac)_2$ (0.420 g, 1.20 mmol) and stir the dark slurry for an additional 5 minutes. Charge this slurry to a mixture of 2-(2,2-dimethylpropylamino)-3-nitro-6-bromopyridine (50.00 g, 173.61 mmol) in toluene (500.00 mL) in a one liter autoclave at ambient temperature. Heat the autoclave to 75° C. in the presence of $H_2$ at 35 psi (2.38 atmospheres) with stirring at 100 rpm. After 3 hours filter the reaction mixture over a Hyflo Super Cel® pad and concentrate the filtrate under reduced pressure to one half of the overall mass (273.0 g) of the solution. Stir the solution and add cyanogen bromide (18.4 g, 173.70 mmol) followed by MeOH (250 mL). After 18 h, heat to 40° C. and concentrate under reduced pressure until 350 mL of solvent is collected via short path distillation. Dilute the resulting slurry with MTBE (350 mL, 7.0 vol.), cool to 0° C., and stir 1 h. Filter off solid, wash with MTBE (75 ml, 1.5 vol.), and dry under reduced pressure at 40° C. for 24 h to provide 48.06 g (76%) of the desired compound as a white solid.

$^1$H-NMR (300 MHz, DMSO-$d_6$): δ 0.96 (9H, s), 3.91 (2H, s), 7.45 (1H, d, J=8.1 Hz), 7.64 (1H, d, J=8.1 Hz), 8.73 (2H, bs).

MS (ES−): m/z=282.0; (M−1)$^−$ 3-(2,2-Dimethyl-propyl)-5-(4-fluoro-phenylethyl)-3H-imidazo[4,5-b]pyridin-2-ylamine Add triethylamine (27.10 g, 267.80 mmol) to a mixture of 5-bromo-3-(2,2-dimethyl-propyl)-3H-imidazo[4,5-b]pyridin-2-yl-ammonium bromide (25.00 g, 68.67 mmol) in ethanol (25 mL) and toluene (75 mL). Heat to 70-75° C. and then add Pd(OAc)$_2$ (0.15 g, 0.69 mmol), triphenylphosphine (0.72 g, 2.75 mmol), and copper (I) iodide (0.13 g, 0.69 mmol). Add ⅔ of a solution of 4-fluorophenylacetylene (12.37 g, 103.00 mmol) in toluene (50 mL, 2.0 vol.) over 15 minutes. Add the remaining 4-fluoroacetylene solution after 1 h. After 3 h, add additional 4-fluorophenylacetylene (1.5 g, 12.86 mmol). After an additional hour, remove EtOH by distillation. Cool the reaction mixture to <40° C. and add water (25 mL). Cool to room temperature. Filter suspension and wash with water (25 mL) and 2×25 mL toluene. Dry under reduced pressure at 45-50° C. to provide 19.3 g (87%) of the desired compound.

Purification Step

Add methanol (1,200 mL) to combined lots of 3-(2,2-dimethyl-propyl)-5-(4-fluoro-phenylethynyl)-3H-imidazo[4,5-b]pyridin-2-ylamine (37.30 g) and heat to reflux. Add activated charcoal (3.73 g, 10 wt %) and reflux for 1 h. Filter while slurry is hot, then add water (375 mL) to the filtrate with stirring at room temperature. Filter off solids, wash 2×100 mL water and dry under reduced pressure at 45-50° C. to provide 30.0 g (80%) of the desired compound.

$^1$H-NMR (300 MHz, DMSO-$d_6$): δ 0.99 (9H, s), 3.91 (2H, s), 6.98 (2H, s), 7.25-7.32 (3H, m), 7.40 (1H, d, J=7.8 Hz), 7.62-7.67 (2H, m).

1-[2-Amino-3-(2,2-dimethyl-propyl)-3H-imidazo[4,5-b]pyridin-5-yl]-2-(4-fluoro-phenyl)-ethane-1,2-dione Add MgSO$_4$ (82.7 g, 687.05 mmol) and NaHCO$_3$ (14.4 g, 171.41 mmol) in deionized water (1524 mL) over 5 minutes to a stirring solution of 3-(2,2-dimethyl-propyl)-5-(4-fluoro-phenylethynyl)-3H-imidazo[4,5-b]pyridin-2-ylamine (110.76 g, 343.57 mmol) in acetone (3665 mL). Add Hyflo Super Cel® (171.1 g) followed by KMnO$_4$ (108.6 g, 687.21 mmol). Heat at 40-45° C. for 3 hours and then cool to room temperature. Add saturated aqueous Na$_2$SO$_3$ (1,800 mL) followed by EtOAc (3,500 mL) and water (3,500 mL). Filter through bed of Hyflo Super Cel® washing with a mixture of 9% MeOH/EtOAc (2,860 mL). Separate layers of filtrate, back-extract aqueous layer 2×2,750 mL EtOAc. Combine organic extracts, wash 2×2,380 mL saturated aqueous sodium chloride (4760 mL), and dry over Na$_2$SO$_4$. Filter, then concentrate under reduced pressure to provide a dark red-brown solid (185 g). Add acetone (650 mL), filter suspension, wash collected solid 3×167 mL MTBE (501 mL), and dry under reduced pressure at 45° C. to provide 106.79 g (88%) of the desired compound as a light yellow solid.

$^1$H-NMR (500 MHz, DMSO-$d_6$): δ 0.72 (9H, s), 3.71 (2H, s), 7.47 (2H, dd, J=7.5 Hz, J$_2$=8.5 Hz), 7.56 (2H, bs), 7.65 (1H, d, 8.0 Hz), 7.97-7.99 (2H, m), 8.02 (1H, d, J=8.0 Hz).

MS (ES+): m/z=355.4; (M+1)$^+$

5-[2-tert-Butyl-5-(4-fluoro-phenyl)-1H-imidazol-4-yl]-3-(2,2-dimethyl-propyl)-3H-imidazo[4,5-b]pyridin-2-ylamine Heat a mixture of 1-[2-amino-3-(2,2-dimethyl-propyl)-3H-imidazo[4,5-b]pyridin-5-yl]-2-(4-fluoro-phenyl)-ethane-1,2-dione (25.33 g, 71.48 mmol), NH$_4$OAc (82.3 g, 1.04 mol), and trimethyl-acetaldehyde (13.0 mL, 116 mmol), in MeOH (650 mL) to reflux under nitrogen for 20 h. Concentrate under reduced pressure. Dissolve residue in EtOAc (2,000 mL), deionized water (500 mL), and saturated aqueous NaHCO$_3$ (1000 mL). Separate the layers and wash organic layer with 1 L saturated aqueous NaHCO$_3$ (1000 mL), deionized water (500 mL), and saturated aqueous sodium chloride (500 mL), then dry over Na$_2$SO$_4$. Filter and concentrate under reduced pressure to provide 20.08 g of a dark solid/foam. Add MTBE (60 mL) and heat to reflux. Add hexane (290 mL) over 5 min. then cool slurry to room temperature. Stir 1.25 h, filter, wash collected solid with hexane (80 mL), and dry under reduced pressure at 45° C. overnight to provide 17.31 g (58%) of the desired compound as a light tan solid.

Purification Step

Heat a mixture of combined lots of 5-[2-tert-Butyl-5-(4-fluoro-phenyl)-1H-imidazol-4-yl]-3-(2,2-dimethyl-propyl)-3H-imidazo[4,5-b]pyridin-2-ylamine (55.9 g) in MTBE (165 mL) to reflux. Add hexane (800 mL) and cool slurry to room temperature. Filter solid, wash with hexane (200 mL), and dry under reduced pressure at 45° C. to provide 54.35 g (97%) of the desired compound as a light tan solid.

$^1$H-NMR (300 MHz, CD$_3$OD): δ 0.87 (9H, s), 1.45 (9H, s), 3.79 (2H, s), 7.05 (2H, dd, J=8.7 Hz, J$_2$=9.0 Hz), 7.30 (1H, bs), 7.40-7.50 (3H, m).

MS (ES+): m/z=421.4 (M+1)$^+$

5-[2-tert-Butyl-5-(4-fluoro-phenyl)-1H-imidazol-4-yl]-3-(2,2-dimethyl-propyl)-3H-imidazo[4,5-b]pyridin-2-ylamine dimethanesulfonate Heat a solution of 5-[2-tert-Butyl-5-(4-fluoro-phenyl)-1H-imidazol-4-yl]-3-(2,2-dimethyl-propyl)-3H-imidazo[4,5-b]pyridin-2-ylamine (10.0853 g, 23.98 mmol) in MeOH (24 mL) to 40° C. Remove heat source and add methanesulfonic acid (3.14 mL, 47.91 mmol) in EtOAc (10 mL) dropwise over 3.5 minutes. Stir for 1 h while cooling to room temperature. Add EtOAc (20 mL) and stir 5 minutes. Filter, wash solid with 2×50 mL EtOAc, and dry under reduced pressure at 45-50° C. for 2.5 h to provide 12.62 g (86%) of the title compound as a white powder solid.

$^1$H-NMR (500 MHz, CD$_3$OD): δ 0.94 (9H, s), 1.65 (9H, s), 2.73 (6H, s), 3.91 (2H, s), 7.31-7.35 (2H, m), 7.63-7.67 (2H, m), 7.69 (1H, d, J=8.5 Hz), 7.87 (1H, d, J=8.5 Hz).

MS (ES+): m/z=421.5 (M+1)$^+$

EXAMPLE 113

5-[2-tert-butyl-5-(4-fluoro-phenyl)-1H-imidazol-4-yl]-3-(2,2-dimethyl-propyl)-3H-imidazo[4,5-b]pyridin-2-ylamine dimethanesulfonate 2-Amino-3-(2,2-dimethyl-propyl)-5-[2-(4-fluorophenyl)-2-oxo-acetyl]-3H-imidazo[4,5-b]pyridin-1-ium methanesulfonate Heat a mixture of 3-(2,2-dimethyl-propyl)-5-(4-fluoro-phenylethynyl)-3H-imidazo[4,5-b]pyridin-2-ylamine (184.7 g, 0.573 mol), formic acid (923.0 mL), methanesulfonic acid (110.0 g, 1.14 mol), DMSO (224.0 g, 2.87 mol), and 48% HBr (9.7 g, 0.057 mol) at gentle reflux (105-107° C.) with a distillation device overnight. Distill out volatiles (550 mL) under reduced pressure. Cool to about 65° C. and add water (1.2 L) containing $Na_2S_2O_3$ (18.0 g, 0.114 mol) dropwise with rigorous stirring, maintaining the temperature at about 65° C. Cool reaction mixture to ambient (about 3 hours), then in ice bath (about 30 minutes). Filter solid, rinse with water (200 mL), and dry in vacuum oven at about 50° C. to provide 217.0 g (84%) or the desired compound.

$^1$H NMR (300 MHz, DMSO-$d_6$): δ 9.08 (s, 2H); 8.18 (d, J=6.0 Hz, 2H); 7.92-7.98 (m, 3H); 7.40 (t, J=8.0 Hz, 2H); 3.67 (s, 2H); 2.40 (s, 2H); 0.66 (s, 9H).

MS (ES$^+$): m/z=355.4 (M+1)$^+$.

Ring Formation

Heat a mixture of 2-amino-3-(2,2-dimethyl-propyl)-5-[2-(4-fluorophenyl)-2-oxo-acetyl]-3H-imidazo[4,5-b]pyridin-1-ium methanesulfonate (0.62 mol), ethanol (2.5 L), ammonium acetate (500.0 g, 6.2 mol), and trimethyl acetaldehyde (84.0 g, 0.93 mol) at about 70° C. overnight. Evaporate the volatiles. Add ethyl acetate (4.0 L) and water (3.0 L) followed by 1.0 N NaOH (1.2 L) and stir for 20-30 minutes at room temperature. Separate the phases and extract the aqueous phase with ethyl acetate (2.0 L). Combine the ethyl acetate phases, wash twice with 10 volumes of saturated aqueous sodium chloride, treat with Darco (30.0 g, 10% by weight). Filter through a pad of Celite and concentrate the filtrate to about 1.0 L). Add ethanol (2.50 L) and heat to about 65° C. and add methanesulfonic acid (150.0 g, 1.55 mol) in ethyl acetate (500 mL) in fast drops, maintaining the temperature at about 65° C. for 3 hours. Cool the reaction mixture to room temperature with stirring for 2 more hours. Filter the suspension, rinse the solid with ethyl acetate (500 mL), and dry in vacuum oven at about 45° C. to provide 226.0 g of the title compound.

$^1$H-NMR (300 MHz, DMSO-$d_6$): δ 8.99 (s, 2H), 7.90 (d, 1H, J=9.0 Hz); 7.86 (d, 1H, J=9.0 Hz); 7.60 (dd, 2H, J=9.0 Hz), 7.34 (dd, 2H, J=9.0 Hz); 3.68 (s, 2H); 2.35 (s, 6H); 1.51 (s, 9H); 0.71 (s, 9H).

MS (ES$^+$): m/z=421.5 (M+1)$^+$.

EXAMPLE 114

General Procedure for the Preparation of Seed Crystals

A master plate is prepared with 250 μL of the free base of the subject compound in methanol (0.1 M) added to all wells set in a 96 well format. An array of acids is dispensed to each well in one and two molar equivalents. The solvents are evaporated from all 96 wells using a Genevac Series II evaporator leaving solid residue in the master plate. An array of solvents is dispensed to each one of these wells through a cap mat and then heated to 55° C. with stirring and allowed to equilibrate for 60-90 minutes at about 55° C. Each sample is then filtered hot and transferred to corresponding wells in an evaporation plate, a precipitation plate, and a cooling plate. The evaporation plate is prepared by transferring 200 μL of the filtrate from the master plate using 55° C. heated syringes to the open well titer plate and is then allowed to evaporate to dryness over night at room temperature and ambient humidity. The precipitation plate is prepared by adding 100 μL of the filtrate from the master plate using 55° C. heated syringes to capped 96 well titer plate where each well contains an anti-solvent of 200 μL of heptane or 2-propanol. After equilibrating for a period of nine hours at room temperature, the excess solution is wicked away using pre-cut Whatman filter paper. The cooling plate is prepared by transferring 200 μL of the filtrate from the master plate to individual wells using 55° C. heated syringes in a capped titer plate, and cooling exponentially from 55 to 10° C. over a period of 8 hours. Photomicrographs are collected on the material at the bottom of each well in the 96 well plates using a Zeiss Axiovert 200M inverted incident-light microscope with a 2.5× objective. If the material is crystalline, it exhibits birefringence that is displayed as white against a dark background. Amorphous solids appear dark or as opaque droplets or rings.

Inhibition of p38 Kinase

Standard Solution Preparations

The kinase buffer solution is prepared by combining 2.5 mL 1 M Tris-HCl (pH 7.5), 0.1 ml 1 M dithiothreitol, 1.0 mL 1 M magnesium chloride, and 300 μL 1% Triton X-100 and diluting to 100 mL with water. 84 mL of this kinase buffer solution is combined with 16 mL DMSO to prepare the 16% DMSO solution.

The 200 μM ATP solution is prepared by adding 102.6 μL 10 mM aqueous ATP, 25 μL $^{33}$P-ATP, and 163.5 μL of 4 mM aqueous Epidermal Growth Factor Peptide 661-681 (Biomol, Catalog #P-121) in 5 mL kinase buffer solution.

The p38 kinase enzyme solution is prepared by dissolving 9.5 μL concentrated enzyme solution (250 ng p38 enzyme/μL kinase buffer solution) in 1536 μL kinase buffer solution.

Sample Preparation

An 80 μM solution of each test compound and control compound are prepared by dissolving 2 μL of a 10 mM stock solution of the respective compounds in dimethylsulfoxide in 248 μL of the 16% DMSO solution in a Costar 96-well microtiter plate. The plate is placed onto the Tecan Genesis automated liquid handler for 1:3 serial dilutions.

Assay

10 μL of serially diluted compound is placed with a Beckmnan Multimek 96-well automated liquid handler to the assay plate. 20 mL of 200 μM ATP solution is added with a Titertek Multidrop 8-channel liquid handler. 10 μL of p38 kinase enzyme solution is transferred to the assay plate using the Multimek. The mixture is allowed to react for min at 30° C. and then the reaction is stopped by adding 60 μL of freshly prepared 5% glacial AcOH with Multidrop. 80 μL of this solution is transferred to an "MAPH" plate using the Multimek. The plates are allowed to set for 30 min at RT and then washed/aspirated on the Titertek MAP extractor with freshly prepared 0.5% glacial AcOH (1×300 μL, 2×200 μL). The wells are blotted and 100 μL MicroScint-20 scintillation fluid (Packard Bioscience) is added with the Multidrop. The plates are allowed to sit for 30 min and counted on a PE/Wallac Microbeta Trilux scintillation counter for $^{33}$P-isotope.

All exemplified compounds were initially tested at 10 concentrations (20 μM–1 nM using 1:3 serial dilutions). Compounds with $IC_{50}$ values less than 25 nM were re-tested at a starting concentration of 2 μM to 0.1 nM (1:3 serial dilutions). $IC_{50}$ values were calculated (IDBS ActivityBase software) for each compound using non-linear regression. All exemplified compounds were tested essentially as described above and were found to inhibit the p38 kinase enzyme with an $IC_{50} \leq 5$ μM. Specifically, the following compounds were tested essentially as described above and were found to inhibit the p38 kinase enzyme as tabulated below.

| Inhibition of TNF-α in vitro | |
|---|---|
| EXAMPLE | $IC_{50}$ (nM) |
| 6 | 7.2 |
| 9 | 4.6 |
| 11 | 2.3 |
| 12 | 3.6 |
| 13 | 3.3 |
| 18 | 3.6 |
| 19 | 3.2 |

Mouse Peritoneal Macrophages 1 mL thioglycolate broth (5.0 g yeast extract, 15.0 g casitone or trypticase, 5.0 g dextrose, 2.5 g sodium chloride, 0.75 g L-cystine, 0.5 g sodium thioglycolate, 1.0 mg resazurin, and 0.75 g agar in 1.0 L distilled water) is injected into the peritoneal cavity of Balb/C female mice. At day 4 or 5 post-injection the mice are sacrificed and then injected i.p. with 4 mL RPMI-1640 medium (BioWhittaker) and the peritoneal macrophages are withdrawn by syringe.

Cytokine Production

Mouse peritoneal microphages are counted with a hemocytometer and adjusted to $5 \times 10^5$ cells/well in 96-well plates in RPMI-1640 medium with 10% fetal bovine serum. 200 μL/well is plated in 96-well plates and the cells allowed to settle and adhere to the bottom of the well for at least 3 h. The test compound or standard p38 kinase inhibitor is pre-treated using a series of 8 concentrations for 1 h at 37° C. (20 μL/well). The cells are treated with a mixture of 50 ng/mL lipopolysaccharide (LPS) and 10 U/mL interferon-γ for 18 h at 37° C. (20 μL/well). The conditioned media is harvested and assayed for TNF-α production using the Luminex procedure.

TNF-α/Luminex Detection Assay (Bio-Rad Bio-Plex Kit—Catalog #171-G12221)

The lyophilized premixed TNF-α standard (1 standard tube/two 96-well plates) is reconstituted with 50 μL sterile water (500,000 pg/mL). The samples are vortexed for 5 seconds, incubated on ice for 30 min, and vortexed for 5 seconds before use. A set of twelve 1.5 mL tubes are labeled with #1-thru #12 and then the amounts of cell media shown below added to the appropriate tubes (standard concentrations are as follows: 50,000; 25,000; 12,500; 6,250; 3,125; 1,562.5; 781.3; 390.6; 195.3; 97.7; 48.8; and 24.4 pg/mL). The premixed anti-cytokine conjugated beads are vortexed (25×) vigorously for 30 seconds. The anti-cytokine conjugated beads are diluted to a 1× concentration using 1× Bio-Plex Assay Buffer. For every plate, 240 μL of the pre-mixed beads is added to 5760 μL of Bio-Plex Assay Buffer. A Millipore 96-well filter plate is blocked with 100 μL/well of blocking buffer. The blocking buffer is filtered through using a Millipore filtration system and then toweled dry. 2 washes are performed on the filter plate with 100 μL/well of Bio-Plex Assay Buffer and toweled dry. The 1× anti-cytokine conjugated beads are vortexed for 15 seconds and added 50 μL to each well. This is filtered through and toweled dry. 2 washes are performed on plates with 100 μl/well of Bio-Plex Wash Buffer. Again, it is filtered through and toweled dry. 50 μL of sample or standard is added to each sample well. This is incubated for 60 seconds at RT on a shaker protected from light at setting 6 and then for 30 min at setting 3 and then placed in the refrigerator overnight. 3 washes are performed with Bio-Plex Wash Buffer. Filter through and toweled dry. The cytokine detection antibody is prepared (~10 min prior to use) for every plate and 60 μL of the premixed cytokine detection antibody stock is added to 5940 μL of Bio-Plex Detection Antibody Diluent. 50 μL of cytokine detection antibody is added and incubated for 60 seconds at RT on a shaker protected from light at setting 6 and then for 30 min at setting 3.3 washes are performed with the Bio-Plex Wash Buffer. This is filtered through and toweled dry. Strept-PE (~10 minutes prior to use) is prepared for every plate and 60 μL to 5940 μL of Bio-Plex Assay Buffer added. 50 μL of Streptavidin-PE is added to each well and incubated for 60 seconds at RT on a shaker protected from light at setting 6 and then for 10 min at setting 3. 3 washes are performed with Bio-Plex Wash-Buffer. This is filtered through. The beads are re-suspended in 100 μL/well of Bio-Plex Assay Buffer. Standards and samples are read on a Luminex machine. These intensity readings are then converted to picogram/milliliter units based on a 12-point standard curve created in duplicate using a four-parameter logistic regression method (Bio-Plex Manager 2.0, Bio-Rad), and the $IC_{50}$ calculated.

Representative members of the exemplified compounds were tested essentially as described above and suppressed TNF-α in vitro with an $IC_{50} < 100$ nM. Specifically, the following compounds were tested essentially as described above and were found to suppress TNF-α in vitro as tabulated below.

| Inhibition of TNF-α in vivo | |
|---|---|
| EXAMPLE | $IC_{50}$ (nM) |
| 6 | <9.1 |
| 9 | 1.2 |
| 11 | 2.4 |
| 13 | <9.1 |
| 18 | <9.1 |
| 19 | <9.1 |
| 104 | 6.3 |

Compounds are administered p.o. (100, 30, 10 and 3 mg/kg) to female Balb/c mice (5 mice/dose). After 2 h, lipopolysaccharide (LPS, E. coli serotype 0111:B4, 5 mg/kg) is administered i.v. in the tail vein of each mouse. One hour after LPS administration the mice are asphyxiated by $CO_2$ inhalation and bled out via cardiac puncture.

TNF-α/Luminex Detection Assay (Bio-Rad Bio-Plex Kit—Catalog #171-G12221)

Reconstitute the lyophilized premixed TNF-α standard (1 standard tube/two 96-well plates) with 50 μL sterile water (500,000 pg/mL). Gently vortex for 5 seconds, incubate on ice for 30 min, and vortex for 5 seconds before use. Label a set of twelve 1.5 mL tubes with #1-thru #12 and then add the amounts of cell media shown below to the appropriate tubes (standard concentrations are as follows: 50,000; 25,000; 12,500; 6,250; 3,125; 1,562.5; 781.3; 390.6; 195.3; 97.7;

48.8; and 24.4 pg/mL). Vortex the premixed anti-cytokine conjugated beads (25×) vigorously for 30 seconds. Dilute the anti-cytokine conjugated beads to a 1× concentration using 1× Bio-Plex Assay Buffer. For every plate, add 240 µL of the pre-mixed beads to 5760 µL of Bio-Plex Assay Buffer. Block a Millipore 96-well filter plate with 100 µL/well of blocking buffer. Filter through the blocking buffer using a Millipore filtration system. Towel dry. Perform 2 washes on the filter plate with 100 µl/well of Bio-Plex Assay Buffer and towel dry. Vortex the 1× anti-cytokine conjugated beads for 15 seconds and add 50 µL to each well. Filter through and towel dry. Perform 2 washes on plates with 100 µl/well of Bio-Plex Wash Buffer. Filter thru and towel dry. Add 25 µL of serum sample and 25 µL of diluent (Bio-Rad) or 50 µL standard to each sample well. Incubate for 60 seconds at RT on a shaker protected from light at setting 6 and then for 30 min at setting 3 and then place in the refrigerator overnight. Perform 3 washes with Bio-Plex Wash Buffer. Filter through and towel dry. Prepare cytokine detection antibody (~10 min prior to use) for every plate, add 60 µL of the premixed cytokine detection antibody stock to 5940 µL of Bio-Plex Detection Antibody Diluent. Add 50 µL of cytokine detection antibody and incubate for 60 seconds at RT on a shaker protected from light at setting 6 and then for 30 min at setting 3. Perform 3 washes with Bio-Plex Wash Buffer. Filter through and towel dry. Prepare strept-PE (~10 minutes prior to use) for every plate, add 60 µL to 5940 µL of Bio-Plex Assay Buffer. Add 50 µL of Streptavidin-PE to each well and incubate for 60 seconds at RT on a shaker protected from light at setting 6 and then for 10 min at setting 3. Perform 3 washes with Bio-Plex Wash Buffer. Filter through. Re-suspend the beads in 100 µL/well of Bio-Plex Assay Buffer. Read standards and samples on Luminex machine. These intensity readings are then converted to picogram/milliliter units based on a 12-point standard curve created in duplicate using a four-parameter logistic regression method (Bio-Plex Manager 2.0, Bio-Rad), and the $IC_{50}$ calculated.

Representative members of the exemplified compounds were tested essentially as described above and suppressed TNF-α in vivo with an $IC_{50}$<100 mg/kg. The compound of EXAMPLE 104 was tested essentially as described above and exhibited an $IC_{50}$<1 mg/kg.

Effect on Intra-articular LPS Induced TNF-α

Intra-articular injection of LPS into rat ankles induces the synthesis of TNF-α, which can be measured in synovial lavage fluid. High levels of TNF-α are detectable within 2 hours. Since the joint is the site where arthritis develops, this model can rapidly determine whether an orally administered compound has an effect on an inflammatory response in the synovium.

Six female Lewis rats (150-200 g) are place in each treatment group. The animals are given vehicle (1% NaCarboxymethylcellulose-0.25% Tween 80) or test compound (1 mg/kg, 3 mg/kg, 10 mg/kg, and 30 mg/kg) orally. One hour later, 10 µl LPS (10 µg) is administered intra-articularly into the right ankle of each rat, while the left ankle receives 10 µL of saline. After two hours, each ankle is lavaged with 100 µL of saline. The lavage is collected and stored at −80° C.
Group#1: Vehicle (1% NaCMC-0.25% Tween 80, 1 mL, PO)
Group#2: Test compound (1 mg/kg, 1 mL, PO)
Group#3: Test compound (3 mg/kg, 1 mL, PO)
Group#4: Test compound (10 mg/kg, 1 mL, PO)
Group#5: Test compound (30 mg/kg, 1 mL, PO)
TNF-α is measured with a commercially available ELISA kit (R&D, RTA00). Treatment with the compound of EXAMPLE 104 produced a dose-dependent inhibition of TNF-α synthesis with $TMED_{50}$ of 0.54 mg/kg.

B16F10 Melanoma Target (MAPKAP-K2 Phosphorylation)

The B16F10 melanoma cell line is obtained from the American Type Culture Collection, Rockville, Md. The cells are cultured in RPMI-1640 medium supplemented with 10% fetal calf serum. The cells grown in vitro are harvested during their exponential growth phase by gentle trypsinization, washed twice in medium, and resuspended in serum-free RPMI-1640 medium. The number of viable cells is determined using a hemocytometer and adjusted to $1\times10^7$/mL. Tumor cells are injected subcutaneously in normal C57B16 mice. Inoculum volume per mouse is 0.2 mL (2,000,000 cells). When the tumors reach 300-500 mg, the mice are used for target inhibition studies at either a fixed time (2.5 hours) after p.o. compound treatment or pharmacodynamic studies where the tumors are collected at multiple time-points (e.g., 3, 6, 9, 12, 15, and 18 h) after p.o. compound treatment.

Protein Extraction and Immuno-Blot Analysis

Tumors collected as described above are immediately snap-frozen in liquid nitrogen and stored at −80° C. Tumor tissues are homogenized on ice using a Daunce homogogenizer in an extraction buffer (25 mM Tris pH 7.5 containing the following protease inhibitors: 10 µg/mL leupeptin, 10 µg/mL soybean tryp-chymotrypsin inhibitor, 10 µg/mL N-tosyl-L-phenylalanine chloromethyl ketone, 10 µg/mL aprotinin, Nα-p-tosyl-L-arginine methyl ester, 7 mM benzamidine, 0.3 mM phenylmethylsulfonyl fluoride and two tablets of Roche complete protease inhibitor cocktail; following phosphatase inhibitors: 60 mM beta-glycerophosphate, 1 mM sodium vanadate, 10 mM sodium fluoride. 20 mM p-nitrophenyl phosphate, 1 PM okadaic acid, 1 µM microcystin, 2.5 mM sodium pyrophoshoate; and 1 mM dithiothreitol, 15 mM EDTA, 5 mM EGTA, 1% Triton X100 and 150 mM NaCl). Tissue lysates are cleared by centrifugation in a refrigerated microcentrifuge at 14,000 rpm and at 1° C. for 20 min. Supernatants are transferred to fresh microfuge tubes prechilled on ice and snap-freeze again in liquid nitrogen or dry ice. After quick thaw to about 80% completion in lukewarm water, the samples are placed on ice to complete thaw. The samples are centrifuged again at 14,000 rpm and at 1° C. for 15 min. The supernatant is transferred to fresh prechilled microfuge tubes and protein concentrations are measured using Bio-Rad protein assay reagents using bovine serum albumin as protein standard.

Protein extracts are equalized with the extraction buffer. An equal volume of 2×SDS sample buffer is added to the protein extracts and boiled in a waterbath for 5 min. 100 µg of protein extract per sample is used for electrophoresis on 4-20% gradient SDS-PAGE gel and transferred onto nitrocellulose (NC) membranes. NC membranes are blocked in 5% BSA in TBST (20 mM Tris pH=7.5, 500 mM NaCl, 0.05% Tween 20 and 0.02% sodium azide) for least 1 h. The membranes are then incubated in primary antibody at 1:1,000 with 5% BSA in TBST overnight on a shaker with 80 rpm at 4° C. Membranes are washed 4×, 10 min each, with TBST. The membranes are then incubated for 40 min with secondary antibody HRP (horse radish peroxidase) conjugate at 1:10,000 dilution in 3% non-fat milk in TBST and washed again 4 times with TBST, 10 min each. The immuno-blots are then visualized by enhanced chemiluminescence (ECL, Amersham) as per manufacturer's instructions. All primary antibodies are purchased from Cell Signaling and secondary antibody HRP conjugates are obtained from Amersham. Gels, membranes and apparatus used for electrophoresis and Western blotting are purchased from Invitrogen. Protein bands of interest are quantified from films using Kodak Image Station 1000.

The compound of EXAMPLE 104 was tested essentially as described above and exhibited a $TMED_{50}=3.59$ mg/kg Rat Collagen Induced Arthritis Efficacy Model Female Lewis rats (≅190 g, Charles River Labs) are immunized with Bovine type II collagen (2 mg/mL) emulsified with an equal volume of adjuvant (aluminum hydroxide). were used. The rats are immunized with approximately 0.3 mg of the emulsion intradermally on the back near the base of the tail. All animals are re-immunized 7 days later according to the same protocol. The rats begin to develop arthritis (characterized by swelling and redness of one or both ankles) from 12 to 14 days after the first immunization. The rats are equally distributed into five treatment groups at the first signs of arthritis and treatment is initiated with each rat dosed bid for 14 days.

Treatment Groups:

| Group 1 | Vehicle (1% NaCarboxymethylcellulose + 0.25% Tween 80) 1 mL, PO, Bid × 14 days |
| Group 2 | Test compound, 5 mg/kg, 1 mL, PO, Bid × 14 |
| Group 3 | Test compound, 15 mg/kg, 1 mL, PO, Bid × 14 |
| Group 4 | Test compound, 30 mg/kg, 1 mL, PO, Bid × 14 |
| Group 5 | Prednisolone 10 mg/kg, 1 mL, PO, qd × 14 |

Ankle diameter is measured with calipers 5 days a week and recorded. Data is expressed as the area under the curve (AUC) generated from the composite inflammation scores and statistical analysis performed. The compound of EXAMPLE 104 was tested essentially as described above and exhibited a $TMED_{50}=1.5$ mg/kg (b.i.d.).

Oral administration of the compounds of the present invention is preferred.

However, oral administration is not the only route or even the only preferred route. For example, transdermal administration may be very desirable for patients who are forgetful or petulant about taking oral medicine, and the intravenous route may be preferred as a matter of convenience or to avoid potential complications related to oral administration. Compounds of Formula I may also be administered by the percutaneous, intramuscular, intranasal or intrarectal route in particular circumstances. The route of administration may be varied in any way, limited by the physical properties of the drugs, the convenience of the patient and the caregiver, and other relevant circumstances (*Remington's Pharmaceutical Sciences*, 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations of the present invention may be determined by methods well known to the skilled artisan.

The tablets, pills, capsules, troches, and the like may also contain one or more of the following adjuvants: binders such as povidone, hydroxypropyl cellulose, microcrystalline cellulose, or gelatin; excipients or diluents such as: starch, lactose, microcrystalline cellulose or dicalcium phosphate, disintegrating agents such as: croscarmellose, crospovidone, sodium starch glycolate, corn starch and the like; lubricants such as: magnesium stearate, stearic acid, talc or hydrogenated vegetable oil; glidants such as colloidal silicon dioxide; wetting agents such as: sodium lauryl sulfate and polysorbate 80; and sweetening agents such as: sucrose, aspartame or saccharin may be added or a flavoring agent such as: peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, hydroxypropyl methylcellulose, polymethacrylates, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used.

The compounds of Formula I are generally effective over a wide dosage range.

For example, dosages per day normally fall within the range of about 0.0001 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

The invention claimed is:

1. A compound of Formula I:

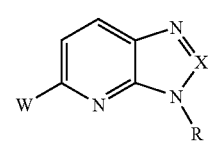

I where:

W is:

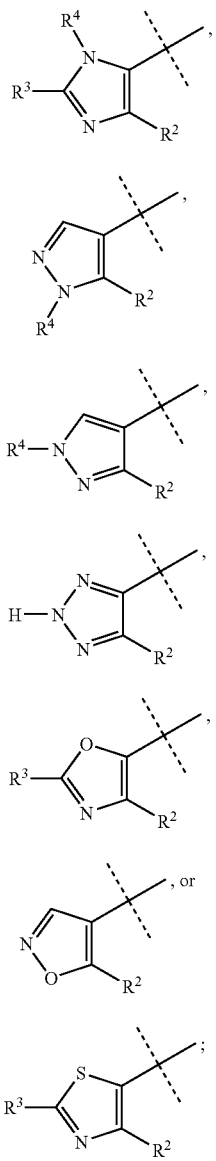

X is N, or C—R$^1$;

R is C$_1$-C$_7$ alkyl, C$_3$-C$_7$ cycloalkyl, (C$_1$-C$_7$ alkylene)-(C$_3$-C$_7$ cycloalkyl), —SO$_2$—(C$_1$-C$_7$ alkyl), or —SO$_2$—NR$^5$R$^6$;

R$^1$ is hydrogen, amino, methyl, or —N=CH(NMe)$_2$;

R$^2$ is phenyl optionally substituted with one or two substituents independently selected from halo;

R$^3$ is hydrogen, C$_1$-C$_7$ alkyl, C$_3$-C$_7$ cycloalkyl, or phenyl optionally substituted with one or two substituents independently selected from halo and trifluoromethyl;

R$^4$ is hydrogen or C$_1$-C$_7$ alkyl;

R$^5$ and R$^6$ are independently selected from the group consisting of C$_1$-C$_7$ alkyl; or a pharmaceutically acceptable salt thereof.

2. A compound of Formula I':

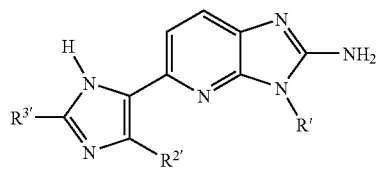

where:
R$^1{'}$ is 2,2-dimethylpropyl or 1,2,2-trimethylpropyl;
R$^{2'}$ is phenyl, 4-fluorophenyl, or 2,4-difluorophenyl;
R$^{3'}$ is tert-butyl, 2-chloro-6-fluorophenyl, 2-fluoro-6-trifluoromethylphenyl, 2,6-dichlorophenyl, or 2,6-difluorophenyl; or a pharmaceutically acceptable salt thereof.

3. The compound of claim 2 wherein
a) R' is 2,2-dimethylpropyl, R$^{2'}$ is 4-fluorophenyl, and R$^{3'}$ is 2-fluoro-6-trifluoromethylphenyl;
b) R' is 2,2-dimethylpropyl, R$^{2'}$ is 4-fluorophenyl, and R$^{3'}$ is 2,6-dichlorophenyl;
c) R' is 2,2-dimethylpropyl, R$^{2'}$ is 4-fluorophenyl, and R$^{3'}$ is tert-butyl;
d) R' is 2,2-dimethylpropyl, R$^{2'}$ is phenyl, and R$^{3'}$ is 2-chloro-6-fluorophenyl;
e) R' is 2,2-dimethylpropyl, R$^{2'}$ is 2,4-difluorophenyl, and R$^{3'}$ is tert-butyl;
f) R' is 1,2,2-trimethylpropyl, R$^{2'}$ is 4-fluorophenyl, and R$^{3'}$ is tert-butyl; or
g) R' is 1,2,2-trimethylpropyl, R$^{2'}$ is 4-fluorophenyl, and R$^{3'}$ is 2,6-difluorophenyl; or a pharmaceutically acceptable salt thereof.

4. The compound of claim 1 which is 5-[2-tert-butyl-5-(4-fluoro-phenyl)-1H-imidazol-4-yl]-3-(2,2-dimethyl-propyl)-3H-imidazo[4,5-b]pyridin-2-ylamine, or a pharmaceutically acceptable salt thereof.

5. A pharmaceutical formulation comprising a compound of Formula I:

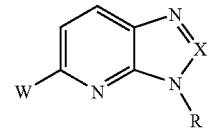

where:
W is:

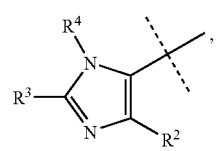

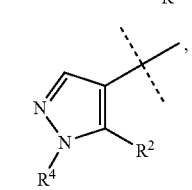

-continued

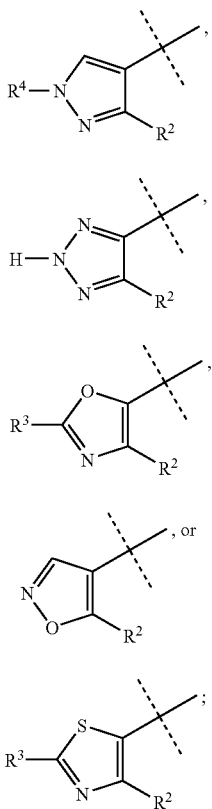

(iii)

(iv)

(v)

(vi), or (vii)

X is N, or C—R$^1$;

R is C$_1$-C$_7$ alkyl, C$_3$-C$_7$ cycloalkyl, (C$_1$-C$_7$ alkylene)-(C$_3$-C$_7$ cycloalkyl), —SO$_2$—(C$_1$-C$_7$ alkyl), or —SO$_2$—NR$^5$R$^6$;

R$^1$ is hydrogen, amino, methyl, or —N=CH(NMe)$_2$;

R$^2$ is phenyl optionally substituted with one or two substituents independently selected from halo;

R$^3$ is hydrogen, C$_1$-C$_7$ alkyl, C$_3$-C$_7$ cycloalkyl, or phenyl optionally substituted with one or two substituents independently selected from halo and trifluoromethyl;

R$^4$ is hydrogen or C$_1$-C$_7$ alkyl;

R$^5$ and R$^6$ are independently selected from the group consisting of C$_1$-C$_7$ alkyl; or a pharmaceutically acceptable salt thereof in combination with a pharmaceutically acceptable carrier, diluent or excipient.

6. A method of inhibiting p-38 kinase in a mammal comprising administering to a mammal in need of such treatment an effective amount of a compound of Formula I:

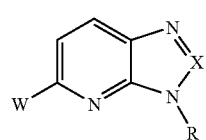

I where:
W is:

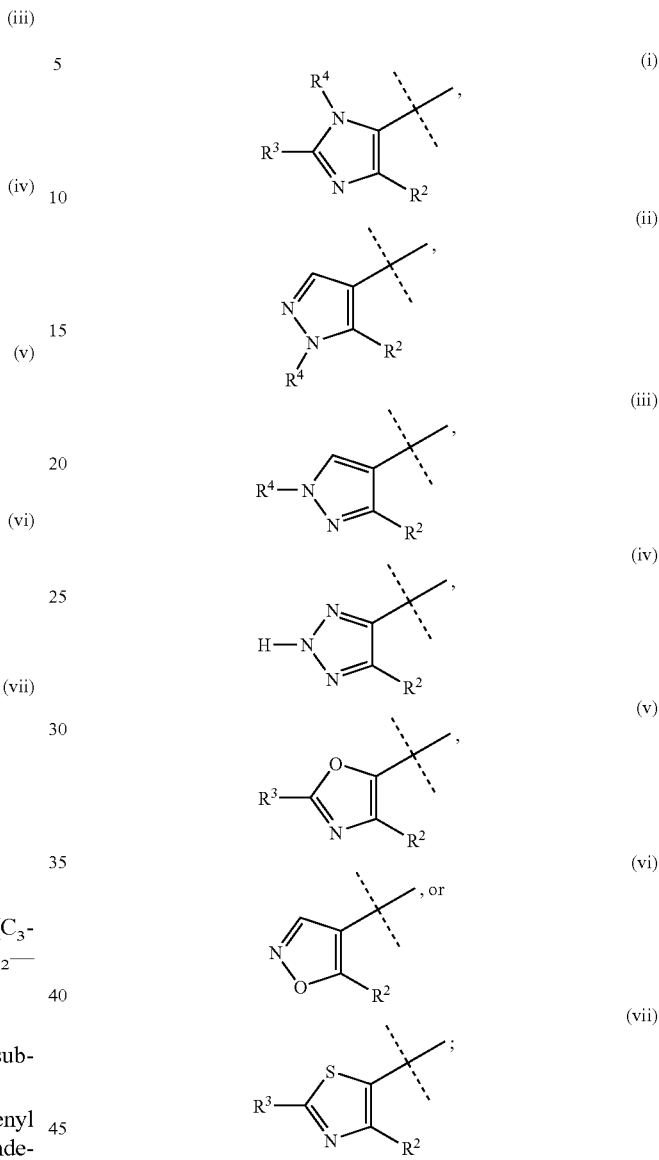

(i)

(ii)

(iii)

(iv)

(v)

(vi), or (vii)

X is N, or C—R$^1$;

R is C$_1$-C$_7$ alkyl, C$_3$-C$_7$ cycloalkyl, (C$_1$-C$_7$ alkylene)-(C$_3$-C$_7$ cycloalkyl), —SO$_2$—(C$_1$-C$_7$ alkyl), or —SO$_2$—NR$^5$R$^6$;

R$^1$ is hydrogen, amino, methyl, or —N=CH(NMe)$_2$;

R$^2$ is phenyl optionally substituted with one or two substituents independently selected from halo;

R$^3$ is hydrogen, C$_1$-C$_7$ alkyl, C$_3$-C$_7$ cycloalkyl, or phenyl optionally substituted with one or two substituents independently selected from halo and trifluoromethyl;

R$^4$ is hydrogen or C$_1$-C$_7$ alkyl;

R$^5$ and R$^6$ are independently selected from the group consisting of C$_1$-C$_7$ alkyl; or a pharmaceutically acceptable salt thereof.

7. The salt of claim 1 which is 5-[2-tert-butyl-5-(4-fluorophenyl)-1H-imidazol-4-yl]-3-(2,2-dimethyl-propyl)-3H-imidazo[4,5-b]pyridin-2-ylamine dimethanesulfonate.

* * * * *

UNITED STATES PATENT AND TRADEMARK OFFICE
CERTIFICATE OF CORRECTION

| | | |
|---|---|---|
| PATENT NO. | : 7,582,652 B2 | Page 1 of 1 |
| APPLICATION NO. | : 10/597283 | |
| DATED | : September 1, 2009 | |
| INVENTOR(S) | : Bonjouklian et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 603 days.

Signed and Sealed this

Fourteenth Day of September, 2010

David J. Kappos
*Director of the United States Patent and Trademark Office*